(12) United States Patent
Bobrowicz et al.

(10) Patent No.: US 8,206,949 B2
(45) Date of Patent: Jun. 26, 2012

(54) PRODUCTION OF GLYCOPROTEINS WITH REDUCED O-GLYCOSYLATION

(75) Inventors: Piotr Bobrowicz, Hanover, NH (US); W. James Cook, Hanover, NH (US); Warren Kett, Darlington, NJ (US)

(73) Assignee: GlycoFi, Inc., Lebanon, NH (US)

( * ) Notice: Subject to any disclaimer, the term of this patent is extended or adjusted under 35 U.S.C. 154(b) by 1013 days.

(21) Appl. No.: 12/084,591

(22) PCT Filed: Nov. 10, 2006

(86) PCT No.: PCT/US2006/043535
§ 371 (c)(1),
(2), (4) Date: May 6, 2008

(87) PCT Pub. No.: WO2007/061631
PCT Pub. Date: May 31, 2007

(65) Prior Publication Data
US 2009/0170159 A1      Jul. 2, 2009

Related U.S. Application Data

(60) Provisional application No. 60/737,108, filed on Nov. 15, 2005.

(51) Int. Cl.
| | |
|---|---|
| C12P 21/06 | (2006.01) |
| C12N 1/15 | (2006.01) |
| C12N 1/19 | (2006.01) |
| A01N 43/78 | (2006.01) |
| C07D 277/26 | (2006.01) |

(52) U.S. Cl. .................. 435/69.1; 435/71.1; 435/254.11; 435/254.2; 435/254.21; 435/254.23; 435/254.3; 435/254.6; 435/255.5; 435/255.6; 435/256.1; 435/256.7; 514/369; 548/183

(58) Field of Classification Search ........................ None
See application file for complete search history.

(56) References Cited

U.S. PATENT DOCUMENTS

| | | |
|---|---|---|
| 5,268,364 A | 12/1993 | Kojima et al. |
| 5,714,377 A | 2/1998 | Tanner et al. |
| 5,871,990 A | 2/1999 | Clausen et al. |
| 6,103,501 A | 8/2000 | Bolme et al. |
| 7,029,872 B2 | 4/2006 | Gerngross et al. |
| 7,105,554 B2 | 9/2006 | Orchard et al. |
| 2002/0068325 A1 | 6/2002 | Ng et al. |
| 2002/0128235 A1 | 9/2002 | Konrad et al. |
| 2003/0186850 A1 | 10/2003 | Clausen et al. |
| 2004/0018590 A1 | 1/2004 | Gerngross et al. |
| 2004/0171826 A1 | 9/2004 | Hamilton |
| 2004/0230042 A1 | 11/2004 | Hamilton |
| 2005/0026266 A1 | 2/2005 | Clausen et al. |
| 2005/0170452 A1 | 8/2005 | Wildt et al. |
| 2005/0208617 A1 | 9/2005 | Bobrowicz et al. |
| 2005/0260729 A1 | 11/2005 | Hamilton |
| 2006/0040353 A1 | 2/2006 | Davidson et al. |
| 2006/0160179 A1 | 7/2006 | Bobrowicz et al. |
| 2006/0211085 A1 | 9/2006 | Bobrowicz |

OTHER PUBLICATIONS

During et al., Plant Molecular Biology, vol. 15 (1990), pp. 281-293, "Synthesis and self-assembly of a functional monoclonal antibody . . . "
Noguchi et al., J. Biochem., vol. 117 (1995), pp. 59-62, "Immunogenicity of N-glycolylneuraminic acid-containing carbohydrate chains . . . "
Benvenuto et al., Plant Molecular Biology, vol. 17 (1991), pp. 865-874, "'Phytoantibodies': a general vector for the expression of immunoglobulin . . . "
Herscovics, Biochim. Biophys. Acta, vol. 1473 (1999), pp. 96-107, "Importance of glycosidases in mammalian glycoprotein biosynthesis"
Varki, Glycobiology, vol. 3 (1993), pp. 97-130, "Biological roles of oligosaccharides: all of the theories are correct".
Caldas et al., Protein Engineering, vol. 13 (2000), pp. 353-360, "Design and synthesis of germline-based hemi-humanized single-chain Fv . . . "
Graddis et al., Current Phamaceut. Biotech., vol. 3 (2002), pp. 285-297, "Designing proteins that work using recombinant technologies".
Moremen et al., Glycobiology, Vo. 4 (1994), pp. 113-125, "Glycosidases of the asparagine-linked oligosaccharide processing pathway".
Nakamura et al., Nucleic Acids Research, vol. 28 (2000), pp. 1, "Codon uage tabulated from international DNA sequence databases: . . . "
Marks et al., J. Mol. Biol., vol. 222 (1991), pp. 581-597, "By-passing immunization: Human antibodies from V-gene libraries . . . "
Putlitz et al., Bio/Technology, vol. 8 (1990), pp. 651-654, "Antibody production in baculovirus-infected insect cells".
Sharp et al., Nucleic Acids Research, vol. 15 (1987), pp. 1281-1295, "The codon adaptation index—a measure of directional synonymous codon usage bias, . . . "
Patel et al., Biochem. J, vol. 285 (1992), pp. 839-845, "Different culture methods lead to differences in glycosylation of a murine IgG . . . "
Outchkourov et al., Protein Exp. & Purification, vol. 24 (2002), pp. 18-24, "Optimization of the expression of equistatin in Pichia pastoris".
Vallee et al., The EMBO Journal, vol. 19 (2000), pp. 581-588, "Crystal structure of a class I alpha-1,2-mannosidase . . . "
Willer et al., Curr. Opin. in Structural Biology, vol. 13 (2003), pp. 621-630, "O-mannosyl glycans: from yeast to novel associations with human disease".
Wilson et al., Biochem. J., vol. 275 (1991), pp. 529-534, "Amino acid distributions around O-linked glycosylation sites".

(Continued)

Primary Examiner — Jeffrey Stucker
Assistant Examiner — Stephen Gucker
(74) Attorney, Agent, or Firm — John David Reilly; Immac J. Thampoe

(57) ABSTRACT

A method is described for producing protein compositions having reduced amounts of O-linked glycosylation. The method includes producing the protein in cells cultured in the presence of an inhibitor of Pmt-mediated O-linked glycosylation and/or in the presence of one or more α-1,2-mannosidases.

14 Claims, 2 Drawing Sheets

OTHER PUBLICATIONS

Woo et al., Protein Exp. & Purification, vol. 25 (2002), pp. 270-282, "Gene optimization is necessary to express a bivalent anti-human anti-T cell . . . "

Wright et al., Trends in Biotechnology, vol. 15 (1997), pp. 26-32, "Effect of glycosylation on antibody function: . . . "

Ho et al., Gene, vol. 77 (1989), pp. 51-59, "Site-directed mutagenesis by overlap extension using the polymerase chain reaction".

Maras et al., J. of Biotechnol., vol. 77 (2000), pp. 255-263, "Molecular cloning and enzymatic characterization of a Trichoderma reesei . . . "

Hiatt et al., Nature, vol. 342 (1989), pp. 76-78, "Production of antibodies in transgenic plants".

Horton et al., Gene, vol. 77 (1989), pp. 61-68, "Engineering hybrid genes without the use of restriction enzymes: . . . "

Goldstein et al., Yeast, vol. 15 (1999), pp. 507-511, "Yeast functional analysis reports: heterologous URA3MX cassettes for gene replacement . . . "

Gentzsch et al., The EMBO Journal, vol. 15 (1996), pp. 5752-5759, "The PMT gene family: protein O-glycosylation in *Saccharomyces cerevisiae* is vital".

Ballou, Gene Expression Technol., vol. 185 (1990), pp. 440-470, "Isolation, characterization, and properties of *Saccharomyces cerevisiae* mnn mutants . . . "

Borrebaeck et al., Immunology Today, vol. 14 (1993), pp. 477-479, "Does endogenous glycosylation prevent the use of mouse monoclonal antibodies . . . "

Davidson et al., Glycobiology, vol. 14 (2004), pp. 399-407, "Functional analysis of the ALG3 gene encoding the Dol-P-Man: . . . "

Duman et al., Biotechnol. Appl. Biochem., vol. 28 (1998), pp. 39-45, "O-mannosylation of Pichia pastoris cellular and recombinant proteins".

Goldstein et al., Yeast, vol. 15 (1999), pp. 1541-1553, "Yeast functional analysis reports: three new dominant drug resistance cassettes . . . "

Jefferis et al., Antibody Eng. Chem. Immunol., vol. 65 (1997), pp. 111-128, "Glycosylation of antibody molecules: structural and functional significance".

Cabanes-Macheteau et al., Glycobiology, vol. 9 (1999), pp. 365-372, "N-glycosylation of a mouse IgG expressed in transgenic tobacco plants".

Choi et al., PNAS, vol. 100 (2003), pp. 5022-5027, "Use of combinatorial genetic libraries to humanize N-linked glycosylation in the yeast Pichia pastoris".

Larrick et al., Human Antibodies & Hybridomas, vol. 2 (1991), pp. 171-189, "Recombinant antibodies".

Cumming et al., Glycobiology, vol. 1 (1991), pp. 115-130, "Glycosylation of recombinant protein therapeutics: . . . "

Lis et al., Eur. J. Biochem., vol. 218 (1993), pp. 1-27, "Protein glycosylation: structural and functional aspects".

Orchard, "Rhodanine-3-acetic acid derivatives as inhibitors . . . ", Bioorg. & Med. Chem. Letters (2004), vol. 14, pp. 3975-3978.

Eneyskaya, "alpha-Mannosidase from Trichodermareesei participates . . . ", Biochem. & Biophys. Res. Comm. (1998), vol. 245, pp. 43-49.

Strahl-Bolsinger, "PMT1, the gene for a key enzyme of protein O-glycosylation . . . ", PNAS (1993), vol. 90, pp. 8164-8168.

PRODUCTION OF GLYCOPROTEINS WITH REDUCED O-GLYCOSYLATION

CROSS REFERENCE TO RELATED APPLICATIONS

This patent application claims benefit of International Patent Application No. PCT/US2006/043535, which was filed 10 Nov. 2006, and U.S. Provisional Application No. 60/737,108, which was filed 15 Nov. 2005.

BACKGROUND OF THE INVENTION (1) Field of the Invention

The present invention relates to compositions and methods for producing proteins having specific glycosylation patterns. In particular, the present invention relates to compositions and methods for producing proteins having reduced O-linked glycosylation.

(2) Description of Related Art

Glycoproteins mediate many essential functions in humans and other mammals, including catalysis, signaling, cell-cell communication, and molecular recognition and association. Glycoproteins make up the majority of non-cytosolic proteins in eukaryotic organisms (Lis and Sharon, 1993, Eur. J. Biochem. 218:1-27). Many glycoproteins have been exploited for therapeutic purposes, and during the last two decades, recombinant versions of naturally-occurring glycoproteins have been a major part of the biotechnology industry. Examples of recombinant glycosylated proteins used as therapeutics include erythropoietin (EPO), therapeutic monoclonal antibodies (mAbs), tissue plasminogen activator (tPA), interferon-β(IFN-β), granulocyte-macrophage colony stimulating factor (GM-CSF), and human chorionic gonadotrophin (hCH) (Cumming et al., 1991, Glycobiology 1:115-130). Variations in glycosylation patterns of recombinantly produced glycoproteins have recently been the topic of much attention in the scientific community as recombinant proteins produced as potential prophylactics and therapeutics approach the clinic.

In general, the glycosylation structures of glycoprotein oligosaccharides will vary depending upon the host species of the cells used to produce them. Therapeutic proteins produced in non-human host cells are likely to contain non-human glycosylation which may elicit an immunogenic response in humans—e.g. hypermannosylation in yeast (Ballou, 1990, Methods Enzymol. 185:440-470); α(1,3)-fucose and β(1,2)-xylose in plants, (Cabanes-Macheteau et al., 1999. Glycobiology, 9: 365-372); N-glycolylneuraminic acid in Chinese hamster ovary cells (Noguchi et al., 1995. J. Biochem. 117: 5-62); and, Galα-1,3Gal glycosylation in mice (Borrebaeck, et al., 1993, Immun. Today, 14: 477-479). Carbohydrate chains bound to proteins in animal cells include N-glycoside bond type carbohydrate chains (also called N-glycans; or N-linked glycosylation) bound to an asparagine (Asn) residue in the protein and O-glycoside bond type carbohydrate chains (also called O-glycans; or O-linked glycosylation) bound to a serine (Ser) or threonine (Thr) residue in the protein.

Because the oligosaccharide structures of glycoproteins produced by non-human mammalian cells tend to be more closely related to those of human glycoproteins, most commercial glycoproteins are produced in mammalian cells. However, mammalian cells have several important disadvantages as host cells for protein production. Besides being costly, processes for producing proteins in mammalian cells produce heterogeneous populations of glycoforms, have low volumetric titers, and require both ongoing viral containment and significant time to generate stable cell lines.

It is well recognized that the particular glycoforms on a protein can profoundly affect the properties of the protein, including its pharmacokinetic, pharmacodynamic, receptor-interaction, and tissue-specific targeting properties (Graddis et al., 2002. Curr Pharm Biotechnol. 3: 285-297). For example, it has been shown that different glycosylation patterns of Igs are associated with different biological properties (Jefferis and Lund, 1997, Antibody Eng. Chem. Immunol., 65: 111-128; Wright and Morrison, 1997, Trends Biotechnol., 15: 26-32). It has further been shown that galactosylation of a glycoprotein can vary with cell culture conditions, which may render some glycoprotein compositions immunogenic depending on the specific galactose pattern on the glycoprotein (Patel et al., 1992. Biochem J. 285: 839-845). However, because it is not known which specific glycoform(s) contribute(s) to a desired biological function, the ability to enrich for specific glycoforms on glycoproteins is highly desirable. Because different glycoforms are associated with different biological properties, the ability to enrich for glycoproteins having a specific glycoform can be used to elucidate the relationship between a specific glycoform and a specific biological function of the glycoprotein. Also, the ability to enrich for glycoproteins having a specific glycoform enables the production of therapeutic glycoproteins having particular specificities. Thus, production of glycoprotein compositions that are enriched for particular glycoforms is highly desirable.

While the pathway for N-linked glycosylation has been the subject of much analysis, the process and function of O-linked glycosylation is not as well understood. However, it is known that in contrast to N-linked glycosylation, O-glycosylation is a posttranslational event, which occurs in the cis-Golgi (Varki, 1993, Glycobiol., 3: 97-130). While a consensus acceptor sequence for O-linked glycosylation like that for N-linked glycosylation does not appear to exist, a comparison of amino acid sequences around a large number of O-linked glycosylation sites of several glycoproteins show an increased frequency of proline residues at positions −1 and +3 relative to the glycosylated residues and a marked increase of serine, threonine, and alanine residues (Wilson et al., 1991, Biochem. J., 275: 529-534). Stretches of serine and threonine residues in glycoproteins, may also be potential sites for O-glycosylation.

One gene family that has a role in O-linked glycosylation are the genes encoding the Dol-P-Man:Protein (Ser/Thr) Mannosyl Transferase (Pmt). These highly conserved genes have been identified in both higher eukaryotes such as humans, rodents, insects, and the like and lower eukaryotes such as fungi and the like. Yeast such as *Saccharomyces cerevisiae* and *Pichia pastoris* encode up to seven PMT genes encoding Pmt homologues (reviewed in Willer et al. Curr. Opin. Struct. Biol. 2003 Oct.; 13(5): 621-30.). In yeast, O-linked glycosylation starts by the addition of the initial mannose from dolichol-phosphate mannose to a serine or threonine residue of a nascent glycoprotein in the endoplasmic reticulum by one of the seven O-mannosyl transferases genes. While there appear to be seven PMT genes encoding Pmt homologues in yeast, O-mannosylation of secreted fungal and heterologous proteins in yeast is primarily dependent on the genes encoding Pmt1 and Pmt2, which appear to function as a heterodimer. PMT1 and PMT2 and their protein products, Pmt1 and Pmt2, respectively, appear to be highly conserved among species.

Tanner et al. in U.S. Pat. No. 5,714,377 describes the PMT1 and PMT2 genes of *Saccharomyces cerevisiae* and a method for making recombinant proteins having reduced O-linked glycosylation that uses fungal cells in which one or more of PMT genes have been genetically modified so that recombinant proteins are produced, which have reduced O-linked glycosylation.

Ng et al. in U.S. Published Patent Application No. 20020068325 discloses inhibition of O-glycosylation through the use of antisense or cosuppression or through the engineering of yeast host strains that have loss of function mutations in genes associated with O-linked glycosylation, in particular, one or more of the PMT genes.

UDP-N-acetyl-alpha-D-galactosamine:polypeptide N-acetyl galactosaminyl-transferases (GalNAc-transferases) are involved in mucin type O-linked glycosylation found in higher eukaryotes. These enzymes initiate O-glycosylation of specific serine and threonine amino acids in proteins by adding N-acetylgalactosamine to the hydroxy group of these amino acids to which mannose residues can then be added in a step-wise manner. Clausen et al. in U.S. Pat. No. 5,871,990 and U.S. Published Patent Application No. 20050026266 discloses a family of nucleic acids encoding UDP-N-acetyl-alpha-D-galactosamine:polypeptide N-acetyl galactosaminyl-transferases (GalNAc-transferases). Clausen in U.S. Published Patent Application No. 20030186850 discloses the use of GalNAc-beta-benzyl to selectively inhibit lectins of polypeptide GalNAc-transferases and not serve as substrates for other glycosyltransferases involved in O-glycan biosyntheses, thus inhibiting O-glycosylation.

Inhibitors of O-linked glycosylation have been described. For example, Orchard et al in U.S. Pat. No. 7,105,554 describes benzylidene thiazolidinediones and their use as antimycotic agents, e.g., antifungal agents. These benzylidene thiazolidinediones are reported to inhibit the Pmt1 enzyme, preventing the formation of the O-linked mannoproteins and compromising the integrity of the fungal cell wall. The end result is cell swelling and ultimately death through rupture.

Konrad et al. in U.S. Published Patent Application No. 20020128235 disclose a method for treating or preventing diabetes mellitus by pharmacologically inhibiting O-linked protein glycosylation in a tissue or cell. The method relys on treating a diabetic individual with (Z)-1-[N-(3-Ammoniopropyl)-N-(n-propyl)amino] diazen-ium-1,2-diolate or a derivative thereof, which binds O-linked N-acetylglucosamine transferase and thereby inhibits O-linked glycosylation.

Kojima et al. in U.S. Pat. No. 5,268,364 disclose therapeutic compositions for inhibition of O-glycosylation using compounds such as benzyle-α-N-acetylgalactosamine, which inhibits extension of O-glycosylation leading to accumulation of O-α-GalNAc, to block expression of SLex or SLea by leukocytes or tumor cells and thereby inhibit adhesion of these cells to endothelial cells and platelets.

Boime et al. U.S. Pat. No. 6,103,501 disclose variants of hormones in which O-linked glycosylation was altered by modifying the amino acid sequence at the site of glycosylation.

The present inventors have found that particular chemical compounds that are inhibitors of Pmt proteins, which are generally lethal to fungi, can be used in a way which is not lethal to the host cells for production of recombinant proteins with reduced O-linked glycosylation. This enables O-linked glycosylation of proteins produced from fungi and yeast cells to be controlled. Other classes of chemical compounds, which the inventors believe to be non-lethal inhibitors of the PMT enzymes, are also useful in the production of improved glycoproteins with reduced O-linked glycosylation. The present inventors have further found that addition to the host cell or cell culture of certain classes of enzymes, namely, α-1,2-mannosidases, alone or in combination with a chemical inhibitor of Pmt proteins effects a further reduction of O-glycosylation.

BRIEF SUMMARY OF THE INVENTION

The present invention provides methods for producing proteins and glycoproteins having specific glycosylation patterns. In particular, the present invention provides a method for making a recombinant protein compositions in a host cell in which the O-linked glycosylation of the recombinant protein is reduced by contacting the host cells with one or more inhibitors of Pmt-mediated O-linked glycosylation of proteins in the host cell or contacting the host cells or the recombinant protein with one or more α-1,2-mannosidases, or both. The amount of O-linked glycosylation of the recombinant protein or glycoprotein is reduced compared to the amount of O-linked glycosylation of the recombinant protein or glycoprotein produced by the host cell in the absence of the inhibitor.

Pmt-mediated O-linked glycosylation refers to O-linked glycosylation wherein transfer of mannose residues to the serine or threonine residues of a protein is mediated by a protein-O-D-mannosyltransferase (Pmt) or homologue encoded by a PMT gene or its homologue. The inhibitors of Pmt-mediated O-linked glycosylation include inhibitors that inhibit any one of the homologues of the PMT genes. In a currently preferred aspect, the inhibitor inhibits at least Pmt1 and/or Pmt2 activity of fungi and yeast, or the corresponding homologue in other organisms, including but not limited to, mammals, plants, and insects.

Currently, it is preferable that the amount of O-linked glycosylation has been reduced through the use of a chemical inhibitor, for example, a chemical inhibitor encompassed by the class of chemicals called benzylidene thiazolidinediones. In particular embodiments, the chemical inhibitor is selected from the group consisting of 5-[[3,4-bis(phenylmethoxy) phenyl]methylene]-4-oxo-2-thioxo-3-thiazolidineacetic acid; 5-[[3-(1-Phenylethoxy)-4-(2-phenylethoxy)]phenyl] methylene]-4-oxo-2-thioxo-3-thiazolidineacetic acid; 3-Hydroxy-4-(2-phenylethoxy)benzaldehyde; 3-(1-Phenylethoxy)-4-(2-phenylethoxy)-benzaldehyde; 5-[[3-(1-Phenyl-2-hydroxy)ethoxy)-4-(2-phenylethoxy)]phenyl] methylene]-4-oxo-2-thioxo-3-thiazolidineacetic acid.

In further aspects, provided is a method for producing recombinant protein compositions having reduced O-linked glycosylation, which use one or more inhibitors of the Pmt proteins involved in O-linked glycosylation and/or one or more α-1,2-mannosidase enzymes to produce the protein having reduced O-linked glycosylation. Currently preferred α-1,2-mannosidases may be isolated from eukaryotic cells, including mammalian and yeast cells. In currently preferred embodiments, the α-1,2-mannosidase is that produced by *Trichoderma reesei, Saccharomyces* sp., or *Aspergillus* sp. In other currently preferred embodiments, the α-1,2-mannosidase may be produced from a chimeric construct comprising a nucleic acid sequence encoding the catalytic domain of an α-1,2-mannosidase operatively linked to a nucleic acid sequence encoding a cellular targeting signal peptide not normally associated with the catalytic domain. In other embodiments, the α-1,2-mannosidase may be separately produced and added to the cell culture, or may be produced by co-expressing the α-1,2-mannosidase with the recombinant glycoprotein.

In particular aspects of the method, the recombinant protein composition comprises a glycoprotein having N-linked glycosylation wherein the recombinant glycoprotein includes at least one predominant N-glycoform and has reduced O-linked glycosylation. Therefore, further provided are glycoprotein compositions comprising a predominant species of N-glycan structure and having reduced O-linked glycosylation compared to compositions of the glycoprotein which have been produced in host cells have not been incubated in the presence of an inhibitor of Pmt-mediated O-linked glycosylation or an α-1,2-mannosidase capable of trimming more than one mannose residue from a glycans structure. In particular aspects, the glycoprotein composition comprises a glycoprotein having a predominant N-glycan structure selected from the group consisting of Man$_5$GlcNAc$_2$, Man$_3$GlcNAc$_2$, GlcNAcMan$_5$GlcNAc$_2$, GlcNAcMan$_3$GlcNAc$_2$, GlcNAc$_2$Man$_3$GlcNAc$_2$, GalGlcNAcMan$_5$GlcNAc$_2$, Gal(GlcNAc)$_2$ Man$_5$GlcNAc$_2$, (GalGlcNAc)$_2$Man$_5$GlcNAc$_2$, NANAGalGlcNAcMan$_3$GlcNAc$_2$, NANA$_2$Gal$_2$GlcNAcMan$_3$GlcNAc$_2$, and GalGlcNAcMan$_3$GlcNAc$_2$ glycoforms. An important aspect of the method is that it provides for a glycoprotein composition comprising reduced O-linked glycosylation and predominantly a specific N-linked glycoform in which the recombinant glycoprotein may exhibit increased biological activity and/or decreased undesired immunogenicity relative to compositions of the same glycoprotein produced from mammalian cell culture, such as CHO cells. An additional advantage of producing the glycoprotein composition comprising reduced O-linked glycosylation and a predominant N-linked glycoform is that it avoids production of undesired or inactive glycoforms and heterogeneous mixtures, which may induce undesired effects and/or dilute the more effective glycoform. Thus, therapeutic pharmaceutical composition of glycoprotein molecules comprising, for example, predominantly Man$_5$GlcNAc$_2$, Man$_3$GlcNAc$_2$, GlcNAcMan$_5$GlcNAc$_2$, GlcNAcMan$_3$GlcNAc$_2$, GlcNAc$_2$Man$_3$ GlcNAc$_2$, GalGlcNAcMan$_5$GlcNAc$_2$, Gal(GlcNAc)$_2$ Man$_5$GlcNAc$_2$, (GalGlcNAc)$_2$Man$_5$GlcNAc$_2$, NANAGalGlcNAcMan$_3$GlcNAc$_2$, NANA$_2$Gal$_2$GlcNAcMan$_3$GlcNAc$_2$, and GalGlcNAcMan$_3$GlcNAc$_2$ glycoforms and having reduced O-linked glycosylation may well be effective at lower doses, thus having higher efficacy/potency.

Therefore, provided is a method of producing a protein having reduced O-linked glycosylation comprising providing a nucleic acid encoding a protein; introducing the nucleic acid into a host cell to provide a culture of the host cell; contacting the culture with one or more inhibitors of Pmt-mediated O-linked glycosylation; and isolating the glycoprotein produced by the host cell in the presence of the inhibitor to produce the protein having reduced O-linked glycosylation.

In particular aspects of the method, the culture is grown for a time sufficient to provide a multiplicity of the host cells having the nucleic acid before contacting the culture with the one or more inhibitors of Pmt-mediated O-linked glycosylation or the culture is grown in the presence of the one or more inhibitors of Pmt-mediated O-linked glycosylation at the time the culture is established.

In a further aspect of the method, the nucleic acid encoding the protein is operably linked to an inducible promoter. Then the culture is grown for a time sufficient to provide a multiplicity of the host cells having the nucleic acid before contacting the culture with the one or more inhibitors of Pmt-mediated O-linked glycosylation and an inducer of the promoter to induce expression of the protein and isolating the protein produced by the host cell in the presence of the one or more inhibitors and the inducer to produce the protein having reduced O-linked glycosylation or the culture is contacted with an inducer of the promoter to induce expression of the protein for a time before contacting the culture with the one or more inhibitors of Pmt-mediated O-linked glycosylation and isolating the protein produced by the host cell in the presence of the inhibitor and the inducer to produce the protein having reduced O-linked glycosylation.

Further provided is a method of producing a protein having reduced O-inked glycosylation comprising providing a nucleic acid encoding a protein; introducing the nucleic acid into a host cell to provide a culture of the host cell; contacting the culture with one or more α-1,2-mannosidase enzymes; and isolating the protein produced by the host cell in the presence of the one or more α-1,2-mannosidase enzymes to produce the glycoprotein having reduced O-linked glycosylation.

In particular aspects of the method, the culture is grown for a time sufficient to provide a multiplicity of the host cells having the nucleic acid before contacting the culture with the one or more α-1,2-mannosidase enzymes cosylation. In other aspects, the culture is grown in the presence of the one or more α-1,2-mannosidase enzymes.

In further aspects of the method, a second nucleic acid encoding the one or more α-1,2-mannosidase enzymes is provided and introducing the second nucleic acid into the host cell. In particular aspects, a second nucleic acid encoding the one or more α-1,2-mannosidase enzymes operably linked to an inducible promoter is provided and introducing the second nucleic acid into the host cell and the culture is grown for a time sufficient to provide a multiplicity of the host cells before inducing expression of the protein and the one or more α-1,2-mannosidase enzymes to produce the protein having reduced O-linked glycosylation or expression of the protein is induced for a time before inducing expression of the one or more α-1,2-mannosidase enzymes to produce the protein having reduced O-linked glycosylation or expression of the one or more α-1,2-mannosidase enzymes is induced for a time before inducing expression of the protein to produce the protein having reduced O-linked glycosylation.

Further provided is a method of producing a protein having reduced O-linked glycosylation comprising providing a nucleic acid encoding a protein operably linked to an inducible promoter; introducing the nucleic acid into a host cell and growing the host cell containing the nucleic acid to produce a culture of the host cell; contacting the culture with one or more inhibitors of Pmt-mediated O-linked glycosylation and one or more one or more α-1,2-mannosidase enzymes; and isolating the glycoprotein produced by the host cell in the presence of the one or more inhibitors and the one or more one or more α-1,2-mannosidase enzymes to produce the protein having reduced O-linked glycosylation.

In particular aspects of the method, the culture is grown for a time sufficient to provide a multiplicity of the host cells having the nucleic acid before contacting the culture with the one or more inhibitors of Pmt-mediated O-linked glycosylation or the culture is grown in the presence of the one or more inhibitors of Pmt-mediated O-linked glycosylation at the time the culture is established.

In a further aspect of the method, the nucleic acid encoding the protein is operably linked to an inducible promoter. Then the culture is grown for a time sufficient to provide a multiplicity of the host cells having the nucleic acid before contacting the culture with the one or more inhibitors of Pmt-mediated O-linked glycosylation and an inducer of the promoter to induce expression of the protein and isolating the protein produced by the host cell in the presence of the one or more inhibitors and the inducer to produce the protein having reduced O-linked glycosylation or the culture is contacted with an inducer of the promoter to induce expression of the protein for a time before contacting the culture with the one or more inhibitors of Pmt-mediated O-linked glycosylation and isolating the protein produced by the host cell in the presence of the inhibitor and the inducer to produce the protein having reduced O-linked glycosylation.

In particular aspects of the method, the culture is grown for a time sufficient to provide a multiplicity of the host cells having the nucleic acid before contacting the culture with the one or more α-1,2-mannosidase enzymes. In other aspects, the culture is grown in the presence of the one or more α-1,2-mannosidase enzymes.

In further aspects of the method, a second nucleic acid encoding the one or more α-1,2-mannosidase enzymes is provided and introducing the second nucleic acid into the host cell. In particular aspects, a second nucleic acid encoding the one or more α-1,2-mannosidase enzymes operably linked to an inducible promoter is provided and introducing the second nucleic acid into the host cell and the culture is grown for a time sufficient to provide a multiplicity of the host cells before inducing expression of the protein and the one or more α-1,2-mannosidase enzymes to produce the protein having reduced O-linked glycosylation or expression of the protein is induced for a time before inducing expression of the one or more α-1,2-mannosidase enzymes to produce the protein having reduced O-linked glycosylation or expression of the one or more α-1,2-mannosidase enzymes is induced for a time before inducing expression of the protein to produce the protein having reduced O-linked glycosylation.

In further aspects of the above methods that use one or more inhibitors of a Pmt protein, currently, it is preferred that the one or more inhibitors is selected from the class of molecules comprising benzylidene thiazolidinediones. Currently, it is preferable that the one or more inhibitors be selected from the group consisting of 5-[[3,4-bis(phenylmethoxy)phenyl]methylene]-4-oxo-2-thioxo-3-thiazolidineacetic Acid; 5-[[3-(1-Phenylethoxy)-4-(2-phenylethoxy)]phenyl]methylene]-4-oxo-2-thioxo-3-thiazolidineacetic Acid; and 5-[[3-(1-Phenyl-2-hydroxy)ethoxy)-4-(2-phenylethoxy)]phenyl]methylene]-4-oxo-2-thioxo-3-thiazolidineacetic Acid.

In particular aspects of the above methods that use an α-1,2-mannosidase, it is currently preferable that the α-1,2-mannosidase is selected from the group consisting of *Trichoderma reesei, Saccharomyces* sp., and *Aspergillus* sp. Currently, it is preferable that the α-1,2-mannosidase is from *Trichoderma reesei*. Alternatively, the host cell can include in addition to the first nucleic acid encoding the protein or glycoprotein, a second nucleic acid, which encodes the α-1,2-mannosidase, operably linked to an inducible promoter. Expression of the α-1,2-mannosidase and the protein or glycoprotein can be induced simultaneously or expression of the protein or glycoprotein induced before expression of the α-1,2-mannosidase or vice versa.

While the method can be performed using any host cell that produced proteins having O-linked glycosylation, in currently preferred aspects, the host cell is a lower eukaryotic cell, preferably a fungal cell or a yeast cell. Currently, it is preferred that the host cell be selected from the group consisting of cells from *K. lactis, Pichia pastoris, Pichia methanolica*, and *Hansenula*. In further embodiments for producing recombinant glycoproteins in particular, the host cell is a yeast or filamentous fungal cell that has been genetically modified to produce glycoproteins with predominantly a particular N-glycan structure. In particularly preferred aspects, the host cells are genetically modified so that they express recombinant glycoproteins in which the glycosylation pattern is human-like or humanized. In particular, the host cells can be modified so that they express recombinant glycoproteins having predominantly a particular desired N-glycan structure. A lower eukaryotic host cell when used herein in connection with glycosylation profiles, refers to any eukaryotic cell which ordinarily produces high mannose containing N-linked glycans, and thus, includes most typical lower eukaryotic cells, including uni- and multi-cellular fungal and algal cells.

All publications, patents, patent applications, and other references mentioned herein are hereby incorporated by reference in their entireties.

DETAILED DESCRIPTION OF THE INVENTION

Figure 1:
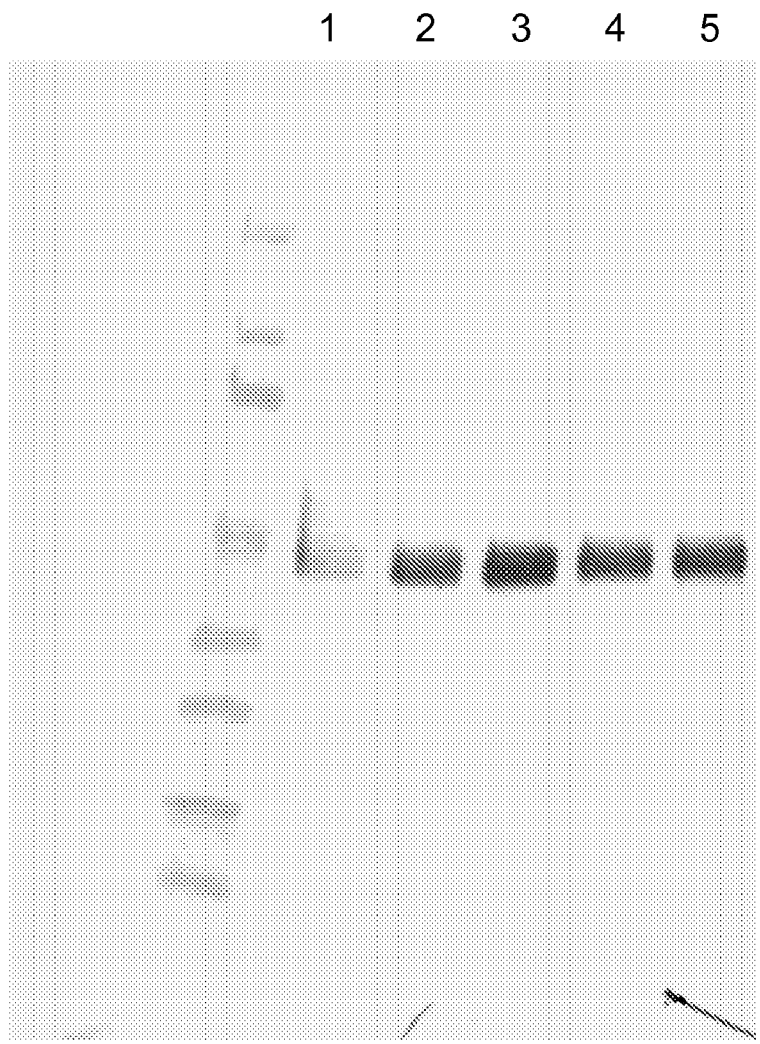
FIG. 1 illustrates the effect of Pmt inhibitors on O-glycosylation of secreted recombinant reporter proteins in *Pichia pastoris*. The chemical inhibitors of Pmt reduced O-glycosylation to a level similar to that observed in a strain lacking PMT1. Western blotting using an anti-polyhistidine antibody was used to detect His-tagged human Kringle 1-3 domain (K1-3) of human plasminogen in the growth media of wild-type (lanes 1-3) and pmt1 (lanes 4-5) strains. The slower migrating bands (seen as a higher molecular weight smear for K1-3 in lane 1) indicate O-glycosylated protein. Pmti-1, PMT inhibitor 1.

The present invention provides a method for expressing a recombinant protein (includes polypeptides and glycoproteins), which is susceptible to O-linked glycosylation in a particular host cell, having a reduced amount of O-linked glycosylation (including no O-linked glycosylation) in that cell type. The method involves inducing expression of a protein of interest in a host cell in which the protein is susceptible to O-linked glycosylation in the host cell in the presence of a chemical inhibitor of the activity of one or more of the Dol-P-Man:Protein (Ser/Thr) Mannosyl Transferase (Pmt) proteins involved in the transfer of mannose to a serine or threonine residue of the protein in the cell or one or more α 1,2-mannosidases, or both, at the time expression of the protein is induced. The protein that is expressed in the presence of the inhibitor or the one or more α 1,2-mannosidases has a reduced amount of O-linked glycosylation compared to the amount of O-linked glycosylation that would have been present on the protein if it had been produced in the absence of the inhibitor or the one or more α 1,2-mannosidases, or both. The method is particularly useful because it provides a means for producing therapeutically relevant proteins where it is desired that the protein have a reduced amount of O-glycosylation in host cells such as lower eukaryotes, for example yeast, and bacteria, which would normally produce proteins with O-linked glycans, having a reduced number of O-linked glycans. However, while the method is especially suitable for expressing proteins with reduced O-linked glycosylation in lower eukaryotic organisms, the method can also be practiced in higher eukaryotic organisms and bacteria.

The method is an improvement over prior art methods for producing proteins having reduced O-linked glycosylation in host cells in which the proteins are susceptible to O-linked glycosylation. For example, Tanner et al. in U.S. Pat. No.

5,714,377 describes a method for making recombinant proteins having reduced O-linked glycosylation using fungal cells such as yeast cells in which one or more of PMT genes encoding the Pmt protein have been genetically modified so that recombinant proteins are produced, which have reduced O-linked glycosylation. While deletion of either the PMT1 or PMT2 genes in a fungal host cell enables production of a recombinant protein having reduced O-linked glycosylation in the fungal host cell, expression of the PMT1 and PMT2 genes are important for host cells growth and either deletion alone also adversely affects the ability of the fungal host cell to grow thus making it difficult to produce a sufficient quantity of host cells or recombinant protein with a reduced amount of O-linked glycosylation. Deletion of both genes appears to be lethal to the fungal host cell. Therefore, genetic elimination of the PMT1 and PMT2 genes in a host cell would appear to be an undesirable means for producing recombinant proteins having reduced O-linked glycosylation.

In contrast, the PMT genes in the host cells used in the method of the present invention have not been modified or deleted, which enables the host cell to O-glycosylate those proteins that are important for cell growth until which time the activity of the Pmt proteins is inhibited. In general, this enables the host cells to be grown to higher levels than the levels that could be obtained if the PMT genes had been deleted. In addition, in particular embodiments, expression of the recombinant protein in the host cell is controlled by an inducible promoter and the Pmt activity in the host cell is not inhibited or one or more α 1,2-mannosidases added, or both, until expression of the recombinant protein is induced. This enables large quantities of host cells containing a nucleic acid encoding a recombinant protein to be produced in culture before inducing expression of the recombinant protein and adding the Pmt inhibitor and/or one or more α 1,2-mannosidases. This can enable production of larger amounts recombinant protein having reduced O-linked glycosylation to be produced in the culture in a shorter period of time than would occur for host cells which have had one or more PMT genes deleted and grow poorly in culture.

This improvement over the prior art also facilitates the production of glycoproteins having reduced O-linked glycosylation in host cells that have been genetically modified to produce glycoproteins having predominantly a particular N-linked glycan structure but which also O-glycosylate the glycoprotein. Methods for producing a wide variety of glycoproteins having predominantly particular N-linked glycoforms have been disclosed in U.S. Pat. No. 7,029,872 and U.S. Published Application Nos. 20050170452, 20050260729, 20040230042, 20050208617, 20050208617, 20040171826, 20060160179, 20060040353, and 20060211085. Any one of the host cells described in the aforementioned patent and patent applications can be used to produce a glycoprotein having predominantly a particular N-linked glycan structure and having reduced O-linked glycosylation using the method disclosed herein. It has been found that some host cells that have been genetically modified to produce glycoproteins having predominantly a particular N-linked glycan structure can grow less well in culture under particular conditions than host cells that have not been modified. For example, particular fungal and yeast cells in which genes involved in hypermannosylation have been deleted and other genes needed to produce particular mammalian or human like N-linked glycan structures have been added, can grow less well than fungal or yeast cells that do not have the genetic modifications. In some of these genetically modified fungal or yeast cells, further introducing deletions of the PMT1 or PMT2 genes either is lethal to the cells or adversely affects the ability of the cells to grow to sufficient quantities in culture. The method herein avoids the potential deleterious effects of deleting the PMT1 and PMT2 genes by allowing the cells to grow to sufficient quantities in culture before inducing expression of the recombinant glycoprotein and adding an inhibitor of the activity of the Pmt proteins, or one or more α 1,2-mannosidases, or both, to produce the recombinant glycoprotein having predominantly particular N-linked glycan structures and reduced O-linked glycosylation.

Therefore, an important aspect of the method is that it provides for a glycoprotein composition comprising reduced O-linked glycosylation and a predominantly a specific N-linked glycoform in which the recombinant glycoprotein may exhibit increased biological activity and/or decreased undesired immunogenicity relative to compositions of the same glycoprotein produced from mammalian cell culture, such as CHO cells. An additional advantage of producing the glycoprotein composition comprising reduced O-linked glycosylation and a predominant N-linked glycoform is that it avoids production of undesired or inactive glycoforms and heterogeneous mixtures, which may induce undesired effects and/or dilute the more effective glycoform. Thus, therapeutic pharmaceutical composition of glycoprotein molecules comprising, for example, predominantly $Man_5GlcNAc_2$, $Man_3GlcNAc_2$, $GlcNAcMan_5GlcNAc_2$, $GlcNAcMan_3$ $GlcNAc_2$, $GlcNAc_2Man_3GlcNAc_2$, $GalGlcNAcMan_5GlcNAc_2$, $Gal(GlcNAc)_2$ $Man_5GlcNAc_2$, $(GalGlcNAc)_2Man_5GlcNAc_2$, $NANAGalGlcNAcMan_3GlcNAc_2$, $NANA_2Gal_2GlcNAcMan_3GlcNAc_2$, and $GalGlcNAcMan_3GlcNAc_2$ glycoforms and having reduced O-linked glycosylation may well be effective at lower doses, thus having higher efficacy/potency.

In general, the method for producing proteins having reduced O-linked glycosylation comprises transforming a host cell with a nucleic acid encoding a recombinant or heterologous protein in which it is desirable to produce the protein having reduced O-linked glycosylation. The nucleic acid encoding the recombinant protein is operably linked to regulatory sequences that allow expression of the recombinant protein. Such regulatory sequences include an inducible promoter and optionally an enhancer upstream, or 5', to the nucleic acid encoding the fusion protein and a transcription termination site 3' or down stream from the nucleic acid encoding the recombinant protein. The nucleic acid also typically encodes a 5' UTR region having a ribosome binding site and a 3' untranslated region. The nucleic acid is often a component of a vector replicable in cells in which the recombinant protein is expressed. The vector can also contain a marker to allow recognition of transformed cells. However, some cell types, particularly yeast, can be successfully transformed with a nucleic acid lacking extraneous vector sequences.

Nucleic acids encoding desired recombinant proteins can be obtained from several sources. cDNA sequences can be amplified from cell lines known to express the protein using primers to conserved regions (see, for example, Marks et al., J. Mol. Biol. 581-596 (1991)). Nucleic acids can also be synthesized de novo based on sequences in the scientific literature. Nucleic acids can also be synthesized by extension of overlapping oligonucleotides spanning a desired sequence (see, e.g., Caldas et al., Protein Engineering, 13, 353-360 (2000)).

In one aspect, the nucleic acid encoding the protein is operably linked to an inducible promoter, which allows expression of the protein to be induced when desired. In another aspect, the nucleic acid encoding the protein is operably linked to a constitutive promoter. To facilitate isolation of the expressed protein, it is currently preferable that the protein include a signal sequence that directs the protein to be excreted into the cell culture medium where it can then be isolated. In the first aspect, the transformed host cells are cultured for a time sufficient to produce a desired multiplicity of host cells sufficient to produce the desired amount of protein before adding one or more inhibitors of Pmt-mediated O-linked glycosylation to the culture medium. The inducer and inhibitor can be added to the culture simultaneously or the inducer is added to the culture before adding the one or more Pmt inhibitors or the one or more Pmt inhibitors is added to the culture before adding the inducer. The induced protein is produced having reduced O-linked glycosylation and can be recovered from the culture medium or for proteins not having a signal sequence, from the host cell by lysis. In the second aspect, wherein the nucleic acid encoding the protein is operably linked to a constitutive promoter, the one or more inhibitors of Pmt-mediated O-linked glycosylation is added to the culture medium at the same time the culture is established and the protein, which is produced having reduced O-linked glycosylation, can be recovered from the culture medium or for proteins not having a signal sequence, from the host cell by lysis. An example illustrating the method using an inducible promoter is shown in Example 2 and an example illustrating the method using a constitutive promoter is shown in Example 3.

Inhibitors useful for producing proteins with reduced O-linked glycosylation are chemicals or compositions that inhibit the activity one or more of the Pmt proteins. When the host cell is a lower eukaryote such as fungi or yeast, it is desirable that the inhibitor inhibit at least the activity of Pmt1 or Pmt2, or both. In higher eukaryotes, it is desirable that the inhibitor inhibit activity of the homologue in the higher eukaryote that corresponds to the Pmt1 or Pmt2. Chemical inhibitors that can be used include the benzylidene thiazolidinediones identified in U.S. Pat. No. 7,105,554, which includes 5-[[3,4-bis(phenylmethoxy)phenyl]methylene]-4-oxo-2-thioxo-3-thiazolidineacetic acid; 5-[[3-(1-phenylethoxy)-4-(2-phenylethoxy)]phenyl]methylene]-4-oxo-2-thioxo-3-thiazolidineacetic acid; 3-hydroxy-4-(2-phenylethoxy)benzaldehyde; 3-(1-phenylethoxy)-4-(2-phenylethoxy)-benzaldehyde; and, 5-[[3-(1-phenyl-2-hydroxy)ethoxy)-4-(2-phenylethoxy)]phenyl]methylene]-4-oxo-2-thioxo-3-thiazolidineacetic acid. Other compounds that might be useful are the structurally similar compounds disclosed in Voss et al. in WO 94/29287, which discloses methods of making arylidene-4-oxo-2-thioxo-3-thiazolidine carboxylic acids and which are disclosed to be useful in the prophylaxis and treatment of late effects of diabetes as well as the prophylaxis and treatment of atherosclerosis and arteriosclerosis and in Esswein et al. in U.S. Pat. No. 6,673,816, which discloses methods of making derivatives of rhodaninecarboxylic acids and their use for treatment of metabolic bone disorders.

In the examples, chemical inhibitors selected from the group consisting of 5-[[3,4-bis(phenylmethoxy)phenyl]methylene]-4-oxo-2-thioxo-3-thiazolidineacetic acid; 5-[[3-(1-phenylethoxy)-4-(2-phenylethoxy)]phenyl]methylene]-4-oxo-2-thioxo-3-thiazolidineacetic acid; and, 5-[[3-(1-phenyl-2-hydroxy)ethoxy)-4-(2-phenylethoxy)]phenyl]methylene]-4-oxo-2-thioxo-3-thiazolidineacetic acid are shown to be effective in producing recombinant proteins having reduced O-linked glycosylation in *Pichia pastoris* strains that had intact, functional PMT1 and PMT2 genes. Table 1 of Example 2 shows that any one of the above three Pmt chemical inhibitors added to a culture of recombinant *Pichia pastoris* having intact, functional PMT1 and PMT2 genes and transformed with a nucleic acid encoding a recombinant, secretable Kringle 1-3 protein operably linked to an inducible promoter at the time expression of the recombinant protein was induced, produced a recombinant protein having a level of reduced O-linked glycosylation that was comparable to the level of O-linked glycosylation seen for *Pichia pastoris* cells containing a deletion of either the PMT1 or PMT2 gene. The above Pmti inhibitors have been used in amounts from about 0.03 µM to 20 µM to produce proteins having reduced O-linked glycosylation compared to the amount of O-linked glycosylation on the protein when grown in similar host cell cultures in the absence of the Pmti inhibitors. The results shown in Example 3 further shows that the host cell cultures can be grown in the presence of Pmti inhibitor at an amount that is sufficient to inhibit O-linked glycosylation without killing the host cells.

The method can include adding to the culture medium containing the one or more Pmt inhibitors one or more α-1, 2-mannosidase enzymes to produce the recombinant protein having reduced O-linked glycosylation. The α-1,2-mannosidases are a conserved family of eukaryotic enzymes for maturation of N-glycans, which are capable of trimming $Man_9GlcNAc_2$ to $Man_8GlcNAc_2$ in yeast. (Vallee et al., 2000, EMBO J., 19: 581-588). The α-1,2-mannosidases are also known as class I α-mannosidases and have been identified in mammalian, lower eukaryotic species, and insect cells (Kawar et al., 2000, Glycobiology 10: 347-355). Mammalian cells are known to have several class I α-mannosidases, some of which are capable of trimming multiple mannose residues (Moremen et al., 1994, Glycobiology 4: 113-125), while yeast appear to have fewer, more specialized α-1,2-mannosidases. For example, *Saccharomyces* has been disclosed to have a single α-1,2-mannosidase encoded by MNN1, which removes one specific mannose residue (for example, $Man_9GlcNAc_2$ to $Man_8GlcNAc_2$) (Herscovics, 1999, Biochim Biophys Acta., 1473: 96-107). Thus, the endogenous α-1,2-mannosidase present in many lower eukaryotes such as fungi and yeast and which cannot remove multiple mannose residues from Glycan structures, is not capable of enabling production of proteins having reduced O-linked glycosylation. Therefore, the method herein requires introduction into the culture medium containing the host cells an α-1,2-mannosidase capable of trimming multiple mannose residues from an O-linked Glycan or introduction into the host cell a nucleic acid encoding an α-1,2-mannosidase capable of trimming multiple mannose residues from an O-linked Glycan. The α-1,2-mannosidase herein includes the intact, native α-1, 2-mannosidase; an α-1,2-mannosidase modified to enhance its α-1,2-mannosidase activity; an α-1,2-mannosidase modified to decrease its α-1,2-mannosidase activity; and, a recombinant α-1,2-mannosidase comprising at least the catalytic domain having the α-1,2-mannosidase activity (for example, a fusion protein comprising the catalytic domain having the α-1,2-mannosidase activity fused to heterologous proteins, polypeptides, or peptides).

In particular embodiments, the α-1,2-mannosidase, which is capable of trimming multiple mannose residues from an O-linked glycans and is added to the cell culture, is produced by *Trichoderma* sp., *Saccharomyces* sp., or *Aspergillus* sp. Currently, preferred α-1,2-mannosidases are obtained from *Trichoderma reesei*, *Aspergillus niger*, or *Aspergillus oryzae*. *T. reesei* is also known as *Hypocrea jecorina*. In Example 3, a transformed yeast comprising an expression cassette, which expresses a recombinant α-1,2-mannosidases comprising the *Trichoderma reesei* α-1,2-mannosidase catalytic domain fused to the *Saccharomyces cerevisiea* αMAT pre signal sequence, was used to produce recombinant proteins having reduced O-linked glycosylation. Another example of a recombinant α-1,2-mannosidase that could be used in the method herein to produce proteins having reduced O-linked glycosylation is the recombinant *Trichoderma reesei* α-1,2-mannosidase disclosed in Maras et al., 2000, J. Biotechnol. 77:255-263 wherein the *Trichoderma reesei* α-1,2-mannosidase catalytic domain was fused to a *Saccharomyces cerevisiea* α-MAT prepro-signal peptide.

The α-1,2-mannosidase can also be produced from a chimeric nucleic acid comprising a nucleic acid sequence encoding at least the catalytic domain of an α-1,2-mannosidase, which is capable of trimming multiple mannose residues from an O-linked glycans, operatively linked to a nucleic acid sequence encoding a cellular targeting signal peptide not normally associated with the catalytic domain. The chimeric nucleic acid can be operably linked to a constitutive or inducible promoter. The chimeric nucleic acid is transformed into a host cell to produce the α-1,2-mannosidase, which is then isolated and then added to the cell culture medium containing cells transformed with the nucleic acid encoding the heterologous protein at the time expression of the protein is induced. Alternatively, the host cell is transformed with the chimeric nucleic acid encoding the α-1,2-mannosidase and the nucleic acid encoding the recombinant protein and co-expressing the α-1,2-mannosidase and the recombinant protein at the same time. In particular embodiments, both the chimeric nucleic acid encoding the α-1,2-mannosidase and the nucleic acid encoding the recombinant protein as both operably linked to an inducible promoter. In other embodiments, one or both of the promoters are constitutive. Example 3 illustrates the method wherein nucleic acids encoding both the α-mannosidase and the recombinant protein are operably linked to a constitutive promoter, introduced into a host cell, and a culture of the host cells is then incubated in the presence of one or more Pmt inhibitors to produce the recombinant protein having reduced O-linked glycosylation. Example 3 further shows that there appears that the Pmti inhibitor and the α-1,2-mannosidase appear to synergistically reduce the amount of O-linked glycosylation compared to the amount of O-linked glycosylation in the presence of either alone.

In particular aspects, reduced O-linked glycosylation can be effected by adding only the one or more α-1,2-mannosidases and not one or more Pmt inhibitors to the culture medium. In one aspect, the nucleic acid encoding the recombinant protein is operably linked to an inducible promoter, which allows expression of the recombinant protein to be induced when desired. In another aspect, the nucleic acid encoding the protein is operably linked to a constitutive promoter. To facilitate isolation of the expressed recombinant protein, it is currently preferable that the protein include a signal sequence that directs the recombinant protein to be excreted into the cell culture medium where it can then be isolated.

In the first aspect, the transformed host cells are cultured for a time sufficient to produce a desired multiplicity of host cells sufficient to produce the desired amount of the recombinant protein before adding the one or more α-1,2-mannosidases to the culture medium. The inducer and the one or more α-1,2-mannosidases can be added to the culture simultaneously or the inducer is added to the culture before adding the one or more α-1,2-mannosidases or the one or more α-1,2-mannosidases is added to the culture before adding the inducer. The induced recombinant protein is produced having reduced O-linked glycosylation and can be recovered from the culture medium or for proteins not having a signal sequence, from the host cell by lysis.

In the second aspect, wherein the nucleic acid encoding the recombinant protein is operably linked to a constitutive promoter, the one or more α-1,2-mannosidases is added to the culture medium at the same time the culture is established and the recombinant protein, which is produced having reduced O-linked glycosylation, can be recovered from the culture medium or for recombinant proteins not having a signal sequence, from the host cell by lysis.

In a further still aspect for producing proteins having reduced O-linked glycosylation without using an inhibitor of Pmt-mediated O-linked glycosylation, the host cell is transformed with a chimeric nucleic acid encoding the α-1,2-mannosidase and a nucleic acid encoding the recombinant protein and co-expressing the α-1,2-mannosidase and the recombinant protein to produce the recombinant protein having reduced O-linked glycosylation. In particular embodiments, both the chimeric nucleic acid encoding the α-1,2-mannosidase and the nucleic acid encoding the recombinant protein as both operably linked to an inducible promoter. In other embodiments, one or both of the promoters are constitutive. In the case of an inducible promoter, the host cells are grown to produce a desired multiplicity of host cells before inducing expression of the α-1,2-mannosidase and/or recombinant protein. Example 3 illustrates the method wherein nucleic acids encoding both the α-1,2-mannosidases and the recombinant protein are operably linked to a constitutive promoter are introduced into a host cell and a culture of the host cells is then incubated for a time to produce the recombinant protein, which has reduced O-linked glycosylation compared to the recombinant protein produced in cells in the absence of the α-1,2-mannosidase.

II. Host Cells

While host cells for the method herein includes both higher eukaryote cells and lower eukaryote cells, lower eukaryote cells, for example filamentous fungi or yeast cells, are currently preferred for expression of proteins because they can be economically cultured, give high yields of protein, and when appropriately modified are capable of producing proteins having suitable glycosylation patterns. Lower eukaryotes include yeast, fungi, collar-flagellates, microsporidia, alveolates (e.g., dinoflagellates), stramenopiles (e.g, brown algae, protozoa), rhodophyta (e.g., red algae), plants (e.g., green algae, plant cells, moss) and other protists. Yeast and fungi include, but are not limited to: *Pichia* sp. (for example, *Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stiptis, Pichia methanolica), Saccharomyces* sp. (for example *Saccharomyces cerevisiea*), *Hansenula polymorpha, Kluyveromyces* sp. (for example, *Kluyveromyces lactis), Candida albicans, Aspergillus* sp (for example, *Aspergillus nidulans, Aspergillus niger, Aspergillus oryzae), Trichoderma reesei, Chrysosporium lucknowense, Fusarium* sp. (for example, *Fusarium gramineum, Fusarium venenatum), Physcomitrella patens* and *Neurospora crassa*. Yeast, in particular, are currently preferred because yeast offers established genetics allowing for rapid transformations, tested protein localization strategies, and facile gene knock-out techniques. Suitable vectors have expression control sequences, such as promoters, including 3-phosphoglycerate kinase or other glycolytic enzymes, and an origin of replication, termination sequences, and the like as desired.

Various yeasts, such as *K. lactis, Pichia pastoris, Pichia methanolica*, and *Hansenula polymorpha* are currently preferred for cell culture because they are able to grow to high cell densities and secrete large quantities of recombinant protein. Likewise, filamentous fungi, such as *Aspergillus* niger, Fusarium sp, Neurospora crass, and others can be used to produce recombinant proteins at an industrial scale.

Lower eukaryotes, in particular filamentous fungi and yeast, can be genetically modified so that they express proteins or glycoproteins in which the glycosylation pattern is human-like or humanized. This can be achieved by eliminating selected endogenous glycosylation enzymes and/or supplying exogenous enzymes as described by Gerngross et al. in U.S. Pat. No. 7,029,872, and U.S. Published Patent Application Nos. 20040018590, 20050170452, 20050260729, 20040230042, 20050208617, 20040171826, 20050208617, 20060160179, 20060040353, and 20060211085. Thus, a host cell can additionally or alternatively be engineered to express one or more enzymes or enzyme activities, which enable the production of particular N-glycan structures at a high yield. Such an enzyme can be targeted to a host subcellular organelle in which the enzyme will have optimal activity, for example, by means of signal peptide not normally associated with the enzyme. Host cells can also be modified to express a sugar nucleotide transporter and/or a nucleotide diphosphatase enzyme. The transporter and diphosphatase improve the efficiency of engineered glycosylation steps, by providing the appropriate substrates for the glycosylation enzymes in the appropriate compartments, reducing competitive product inhibition, and promoting the removal of nucleoside diphosphates. See, for example, Gerngross et al. in U.S. Published Patent Application No. 20040018590 and Hamilton, 2003, Science 301: 1244-46 and the aforementioned U.S. patent and patent applications.

By way of example, a host cell (for example, yeast or fungal) can be selected or engineered to be depleted in 1,6-mannosyl transferase activities, which would otherwise add mannose residues onto the N-glycan of a glycoprotein, and to further include a nucleic acid for ectopic expression of an α-1,2 mannosidase activity, which enables production of recombinant glycoproteins having greater than 30 mole percent $Man_5GlcNAc_2$ N-glycans. When a glycoprotein is produced in the host cells according to the method described herein, the host cells will produce a glycoprotein having predominantly a $Man_5GlcNAc_2$ N-glycan structure and reduced O-glycosylation compared to the glycoprotein produced in the cell otherwise. In a further aspect, the host cell is engineered to further include a nucleic acid for ectopic expression of GlcNAc transferase I activity, which enables production of glycoproteins having predominantly GlcNAcMan5GlcNAc2 N-glycans. When a glycoprotein is produced in the host cells according to the method described herein, the host cells will produce a glycoprotein having predominantly a $GlcNAcMan_5GlcNAc_2$ N-glycan structure and reduced O-glycosylation compared to the glycoprotein produced in the cell otherwise. In a further still aspect, the host cell is engineered to further include a nucleic acid for ectopic expression of mannosidase II activity, which enables production of glycoproteins having predominantly $GlcNAcMan_3GlcNAc_2$ N-glycans. When a glycoprotein is produced in the host cells according to the method described herein, the host cells will produce a glycoprotein having predominantly a $GlcNAcMan_3GlcNAc_2$ N-glycan structure and reduced O-glycosylation compared to the glycoprotein produced in the cell otherwise. In a further still aspect, the host cell is engineered to further include a nucleic acid for ectopic expression of GlcNAc transferase II activity, which enables production of glycoproteins having predominantly $GlcNAc_2Man_3GlcNAc_2$ N-glycans. When a glycoprotein is produced in the host cells according to the method described herein, the host cells will produce a glycoprotein having predominantly a $GlcNAc_2Man_3GlcNAc_2$ N-glycan structure and reduced O-glycosylation compared to the glycoprotein produced in the cell otherwise. In further still aspects, the above host cells can be further engineered to produce particular hybrid or complex N-glycan or human-like N-glycan structures by further including one or more higher eukaryote genes involved in N-linked glycosylation, in any combination, that encode for example, sialytransferase activities, class II and III mannosidase activities, GlcNAc transferase II, III, IV, V, VI, IX activity, and galactose transferase activity. It is currently preferable that the cells further include one or more of nucleic acids encoding UDP-specific diphosphatase activity, GDP-specific diphosphatase activity, and UDP-GlcNAc transporter activity.

Plants and plant cell cultures may be used for expression of proteins and glycoproteins with reduced O-linked glycosylation as taught herein (See, for example, Larrick & Fry, 1991, Hum. Antibodies Hybridomas 2: 172-89); Benvenuto et al., 1991, Plant Mol. Biol. 17: 865-74); Durin et al., 1990, Plant Mol. Biol. 15: 281-93); Hiatt et al., 1989, Nature 342: 76-8). Preferable plant hosts include, for example, *Arabidopsis, Nicotiana tabacum, Nicotiana rustica*, and *Solanum tuberosum.*

Insect cell culture can also be used to produce proteins and glycoproteins proteins and glycoproteins with reduced O-linked glycosylation, as taught herein for example, baculovirus-based expression systems (See, for example, Putlitz et al., 1990, Bio/Technology 8: 651-654).

Although not currently as economical to culture as lower eukaryotes and prokaryotes, mammalian tissue cell culture can also be used to express and produce proteins and glycoproteins with reduced O-linked glycosylation as taught herein (See Winnacker, From Genes to Clones (VCH Publishers, N.Y., 1987). Suitable hosts include CHO cell lines, various COS cell lines, HeLa cells, preferably myeloma cell lines or the like or transformed B-cells or hybridomas. Expression vectors for these cells can include expression control sequences, such as an origin of replication, a promoter, an enhancer (Queen et al., 1986I, mmunol. Rev. 89:49-68), and necessary processing information sites, such as ribosome binding sites, RNA splice sites, polyadenylation sites, and transcriptional terminator sequences. Expression control sequences are promoters derived from immunoglobulin genes, SV40, Adenovirus, bovine Papilloma Virus, cytomegalovirus and the like. Generally, a selectable marker, such as a neoR expression cassette, is included in the expression vector.

The nucleic acid encoding the protein to be expressed can be transferred into the host cell by conventional methods, which vary depending on the type of cellular host. For example, calcium phosphate treatment, protoplast fusion, natural breeding, lipofection, biolistics, viral-based transduction, or electroporation can be used for cellular hosts. Tungsten particle ballistic transgenesis is preferred for plant cells and tissues. (See, generally, Maniatis et al., Molecular Cloning: A Laboratory Manual (Cold Spring Harbor Press, 1982))

Once expressed, the proteins or glycoproteins having reduced O-linked glycosylation can be purified according to standard procedures of the art, including ammonium sulfate precipitation, affinity columns, column chromatography, gel electrophoresis and the like (See, generally, Scopes, R., Protein Purification (Springer-Verlag, N.Y., 1982)). Substantially pure glycoproteins of at least about 90 to 95% homogeneity are preferred, and 98 to 99% or more homogeneity most preferred, for pharmaceutical uses. Once purified, partially or to homogeneity as desired, the proteins can then be used therapeutically (including extracorporeally) or in developing and performing assay procedures, immunofluorescent stainings, and the like. (See, generally, Immunological Methods, Vols. I and II (Lefkovits and Pernis, eds., Academic Press, NY, 1979 and 1981).

Therefore, further provided are glycoprotein compositions comprising a predominant species of N-glycan structure and having reduced O-linked glycosylation compared to compositions of the glycoprotein which have been produced in host cells have not been incubated in the presence of an inhibitor of Pmt-mediated O-linked glycosylation or an α-1,2-mannosidase capable of trimming more than one mannose residue from a glycans structure or both. In particular aspects, the glycoprotein composition comprises a glycoprotein having a predominant N-glycan structure selected from the group consisting of $Man_5GlcNAc_2$, $Man_3GlcNAc_2$, $GlcNAcMan_5GlcNAc_2$, $GlcNAcMan_3GlcNAc_2$, $GlcNAc_2Man_3GlcNAc_2$, $GalGlcNAcMan_5GlcNAc_2$, $Gal(GlcNAc)_2 Man_5GlcNAc_2$, $(GalGlcNAc)_2Man_5GlcNAc_2$, $NANAGalGlcNAcMan_3GlcNAc_2$, $NANA_2Gal_2GlcNAcMan_3GlcNAc_2$, and $GalGlcNAcMan_3GlcNAc_2$ glycoforms.

III. Pharmaceutical Compositions

Proteins and glycoproteins having reduced O-linked glycosylation can be incorporated into pharmaceutical compositions comprising the glycoprotein as an active therapeutic agent and a variety of other pharmaceutically acceptable components (See, Remington's Pharmaceutical Science (15th ed., Mack Publishing Company, Easton, Pa., 1980). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation can also include other carriers, adjuvants, or nontoxic, nontherapeutic, nonimmunogenic stabilizers, and the like.

Pharmaceutical compositions for parenteral administration are sterile, substantially isotonic, pyrogen-free and prepared in accordance with GMP of the FDA or similar body. Glycoproteins can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. Glycoproteins can be administered in the form of a depot injection or implant preparation which can be formulated in such a manner as to permit a sustained release of the active ingredient. Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (See Langer, Science 249, 1527 (1990) and Hanes, Advanced Drug Delivery Reviews 28, 97-119 (1997).

Unless otherwise defined herein, scientific and technical terms and phrases used in connection with the present invention shall have the meanings that are commonly understood by those of ordinary skill in the art. Further, unless otherwise required by context, singular terms shall include the plural and plural terms shall include the singular. Generally, nomenclatures used in connection with, and techniques of biochemistry, enzymology, molecular and cellular biology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, for example, Sambrook et al. Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lane, Antibodies: A Laboratory Manual, Cold Spring Harbor Laboratory Press, Cold Spring Harbor, N.Y. (1990); Taylor and Drickamer, Introduction to Glycobiology, Oxford Univ. Press (2003); Worthington Enzyme Manual, Worthington Biochemical Corp., Freehold, N.J.; Handbook of Biochemistry: Section A Proteins, Vol I, CRC Press (1976); Handbook of Biochemistry: Section A Proteins, Vol II, CRC Press (1976); Essentials of Glycobiology, Cold Spring Harbor Laboratory Press (1999).

The following examples are intended to promote a further understanding of the present invention.

EXAMPLE 1

This example provides method for preparing various Pmt inhibitors. Unless otherwise stipulated all materials were obtained from Sigma-Aldrich Chemical Co. (St. Louis, Mo.) and used as received. The $^1$H NMR spectra of all intermediates and final products were in accord with published data.

Preparation of Pmti-1, (5-[[3,4-bis(phenylmethoxy)phenyl]methylene]-4-oxo-2-thioxo-3-thiazolidineacetic Acid), is as follows.

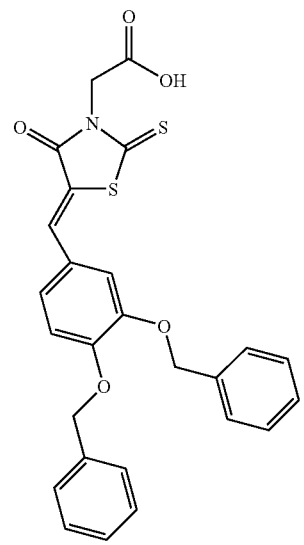

The procedure was adapted from Orchard et al in U.S. Pat. No. 7,105,554. A solution of rhodanine-3-acetic acid (1 g, 5.20 mmol, 1 eq.), 3,4-dibenzyloxybenzaldehyde (2.04 g, 6.25 mmol, 1.2 eq.), and sodium acetate (1.3 g, 15.6 mmol, 3 eq.) in acetic acid (30 mL) is heated to reflux, and stirred overnight. As the reaction mixture is cooled to room temperature, the product is precipitated and filtered and washed with acetic acid, then petroleum ether. The residue is dissolved in hot DMSO, filtered, and precipitated by addition of water. Upon cooling, the precipitate is filtered and recrystallized from ethyl acetate and petroleum ether to give a product which is suspended in water and freeze-dried overnight in vacuo to give the final product as a fluffy yellow powder.

Preparation of Pmti-2, 2 (5-[[3-(1-Phenylethoxy)-4-(2-phenylethoxy)]phenyl]methylene]-4-oxo-2-thioxo-3-thiazolidineacetic Acid), is as follows.

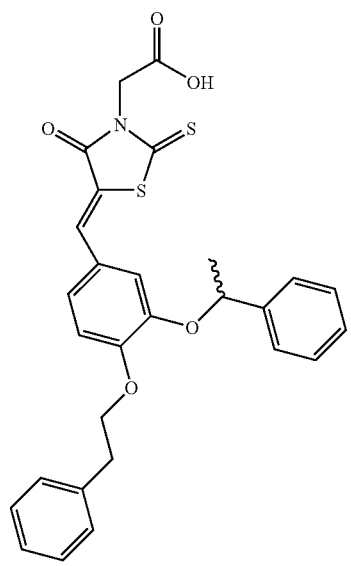

This product is synthesized according to the directions of Orchard et al. in U.S. Pat. No. 7,105,554. A solution of rhodanine-3-acetic acid (375 mg, 1.96 mmol, 1 eq.), 3-(1-phenylethoxy)-4-(2-phenylethoxy)benzaldehyde (680 mg, 1.96 mmol, 1 eq.) and ammonium acetate (453 mg, 3 eq.) is heated to 70° C. for ten minutes, then cooled to room temperature and diluted with ethyl acetate (100 mL). The organic solution is washed with 1M HCl (2×200 mL) and brine (200 mL) then dried over sodium sulfate and evaporated. The product is purified by liquid chromatography using a 10×2.5 cm glass column packed with 35-75 μm C18 (Alltech Associates, Deerfield, Ill.). Gradient elution is employed. Buffer A is 0.1% acetic acid and buffer B is 80% acetonitrile. The gradient is comprised of 20% B for three minutes, increasing to 75% B over 40 minutes. The flow rate is 8 mL/min. Detection is at 280 nm. The appropriate fractions are pooled, concentrated, and freeze-dried in vacuo to give the product as a fluffy yellow powder.

Preparation of Pmti-3, (5-[[3-(1-Phenyl-2-hydroxy)ethoxy)-4-(2-phenylethoxy)]phenyl]methylene]-4-oxo-2-thioxo-3-thiazolidineacetic Acid), (Orchard et al. in U.S. Pat. No. 7,105,554) is synthesized in three steps as follows.

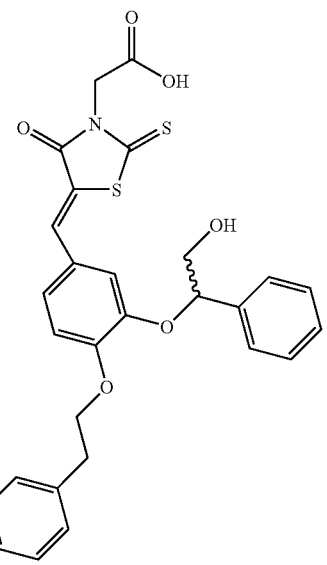

Step 1: Production of (+)-(S)-2-Acetoxy-1-bromo-1-phenylethane. Cold HBr-acetic acid (12.4 g, 52.2 mmol) is added dropwise to (−)-(R)-1-phenylethane-1,2-diol(2.4 g, 17.4 mmol) during about five minutes and the mixture stirred at room temperature for 40 minutes. Water (25 mL) is added and the solution is neutralized with sodium carbonate and extracted with ether (3×30 mL). The combined extracts are dried and evaporated to give (+)-(S)-2-acetoxy-1-bromo-1-phenylethane (3.93 g, 93%), $d^{25}$ 1.415 g/mL, $[x]_0^{24}$+93.5° (c 5.63 in $CCl_4$) 2.72 (5H, s), 4.98 (aH, dd, 6.7 and 7.0 Hz) and 5.56 (2H, d). This product is not distilled. The isomeric homogeneity is established by comparison of the nmr spectrum (absence of PhCH*OAc resonance) with that of 1,2-diacetoxy-1-phenylethane. (Note that racemic reagents are substituted for the optical isomers listed).

Step 2: Production of 3-[(1-Phenyl-2-hydroxy)ethoxy]-4-(2-phenylethoxy)-benzaldehyde. (2-Acetoxy-1-bromoethyl)benzene (3.32 g, 13.67 mmol, 1.2 eq) (the product of Step 1), is added to a stirred solution of 3-hydroxy-4-(2-phenylethoxy)-benzaldehyde (2.76 g, 11.39 mmol, 1 eq.) and cesium carbonate (2.97 g, 9.11 mmol, 0.8 eq.) in N,N-dimethylformamide (15 mL). The solution is stirred for 19 hours at room temperature, then 21 hours at 80° C. The reaction is worked up by partitioning between ethyl acetate and water (brine is added to help break up the emulsion that formed). The organic layer is washed twice more with water, brine, and then dried over sodium sulfate and evaporated to give a dark oil. The residue is purified by chromatography on silica gel and elution with diethyl ether gives an orange oil. This oil is dissolved in methanol (100 ml) and to the solution is added an aqueous solution of sodium hydroxide (7 mL, 1M). After 30 minutes, the mixture is evaporated (to remove the methanol) and the residue partitioned between dichloromethane and water. The organic layer is dried over sodium sulfate and evaporated. The residue is purified by chromatographed on silica gel and elution with petroleum ether:diethyl ether (1:2) gives the product as a cream coloured powder.

Step 3: Production of Pmti-3. A solution of rhodanine-3-acetic acid (158 mg, 0.828 mmol, 1 eq.), 3-(1-phenyl-2-hydroxy)ethoxy)-4-(2-phenylethoxy)benzaldehyde (300 mg, 0.828 mmol, 1 eq.) (the product of Step 2), and ammonium acetate (191 mg, 3 eq) in toluene (10 mL) is heated to reflux for 3.5 hours, cooled to room temperature, and diluted with ethyl acetate (50 mL). The organic solution is washed with 1M HCl (2×200 mL) and brine (200 mL) then dried over sodium sulfate and evaporated. After work-up, the residue is purified by chromatography on silica gel. Elution with ethyl acetate gives a yellow gum, which is recrystallized from diethyl ether and petroleum ether to give the product as a yellow powder.

EXAMPLE 2

This example shows that *Pichia pastoris* transformed with an expression vector encoding the Kringle 1-3 marker glycoprotein and treated with Pmt inhibitors produced a glycoprotein having reduced O-glycosylation.

Plasmid DNA encoding a His-tagged reporter glycoprotein consisting of human plasminogen domains K1, K2, and K3 (Kringle 1-3 protein) under the control of the *Pichia pastoris* alcohol oxidase 1 (AOX1) promoter was transformed into wild-type *Pichia pastoris* to produce strain yJC53. The Kringle reporter protein consisting of domains K1, K2, K3, and K4 has been discussed in Duman et al. Biotechnol. Appl. Biochem. (1998), v.28, p. 39-45 and only domain K3 in Choi et al., 2003, Proc. Natl. Acad. Sci. U.S.A. 100(9): 5022-5027. The amino acid sequence of the Kringle 1-3 protein used in the Example is SECKTGNGKNYRGTMSKTKNGITCQK-WSSTSPHRPRFSPATHPSEGLEENYCRNPDNDPQGP-WCYTTDPEKRYDYCDILECEEECMHCSGENYDGKIS-KTMSGLECQAWDSQSPHAHGYIPSKFPNKNLKKNY-CRNPDRELRPWCFTTDPNKRWELCDIPRCTTPPPSS-GPTYQCLKGTGENYRGNVAVTVSGHTCQHWSAQTP-HTHSRTPENFPCKNLDENYCRNPDGKRAPWCHTTN-SQVRWEYCKIPSCDSSPVSTEQLAPTAPPELTPVVQD-GGGHHHHHHHHH (SEQ ID NO: 1). The Kringle 1-3 protein contains at least two potential mammalian O-glycosylation sites that conform to the purported consensus sequence P at −1 and +3: the serine residue, which is O-glycosylated, is capitalized in the amino acid sequence "pppSsgp" and the threonine residue, which is O-glycosylated, is capitalized in the amino acid sequence "lapTapp". The O-glycosylation sites are underlined in the above amino acid sequence. The potential mammalian O-glycosylation sites are located between the K1 and K domains and the K2 and K3 domains. However, as shown in Table 1, in yeast the protein has about 20 O-linked glycosylation sites. Thus, O-linked glycosylation can be a significant disadvantage to producing proteins in yeast without inhibiting O-linked glycosylation as shown by the methods herein. An N-glycosylation site resides in the K3 domain, which had been removed by replacing the asparagine at position 208 of SEQ ID NO: 1 with a serine. Therefore, the only glycans on the Kringle 1-3 protein would be the result of O-glycosylation.

Plasmid containing DNA encoding the Kringle 1-3 protein was prepared using forward primer K1-3/UP 5'-CGGAA TTCTC AGAGT GCAAG ACTGG GAATA GAA-3' (SEQ ID NO:2) and reverse primer K1-3/LP1 (Reverse primer, 3Gly+2H is, paired with K1-3/UP) 5'-ATGAT GATGA CCACC ACCGT CCTGG ACCAC AGGGG TTAG-3' (SEQ ID NO:3) to produce a PCR product, which was then PCR amplified using reverse primer K1-3/LP2 (Reverse primer, 3Gly+9His+stop codon, paired with K1-3/UP) 5'-TTAAT GATGA TGATG ATGAT GATGA TGATG ACCAC CACC-3' (SEQ ID NO:4). PCR conditions were as follows: after 1 cycle of 95° C. for 2 minutes as a denaturation step, the PCR reaction was subjected to 30 cycles of 95° C. for 30 seconds, 60° C. for 30 seconds, and 72° C. for 1 minute, and then 1 cycle of 72° C. for 10 minutes. After the PCR reaction and column purification of the PCR products, nucleotide A overhangs of the PCR products were generated using ExTaq (1 cycle of 72° C. for 15 minutes). The resulting PCR products were used for the second PCR reaction as a PCR template where the primers, K1-3/UP and K1-3/LP2, were used to amplify wild-type Kringle 1-3+3Gly+9His, which was cloned into a pCR2.1 plasmid vector (Invitrogen) to produce pBK105. The following PCR primers were then used to generate an Asn to Ser mutation at position 208 in the Kringle 1-3 protein to produce amino acid sequence NRTP from amino acid sequence SRTP: forward primer K3f (Asn to Ser) 5'-AC-CCCTCACACACATTCTAGGACACCAGAAAACTTC-3' (SEQ ID NO:5) and reverse primer K3r 5'-CTGTGCACTC-CAGTGCTGACAGGTGTG-3' (SEQ ID NO:6). The Asn to Ser mutation was then generated in pBK105 by the Inverse PCR. PCR conditions were as follows; after 1 cycle of 95° C. for 2 minutes as a denaturation step, the PCR reaction was subjected to 35 cycles of 95° C. for 30 seconds, 60° C. for 30 seconds, and 72° C. for 5 minutes, and then 1 cycle of 72° C. for 10 minutes. The resulting PCR products were ligated to produce plasmid pBK118, which was sequenced to confirm the mutation.

Plasmid pBK118 was digested with EcoRI and the DNA fragments were gel purified and cloned into the EcoRI sites of pPICZaA (Invitrogen, La Jolla, Calif.) to produce pBK119 (*Pichia* expression plasmid). Plasmid pPICZaA contains an α-factor secretion signal that allows the efficient secretion of most proteins from *Pichia pastoris*; 5'-AOX, a 942 bp fragment containing the AOX 1 promoter that allows methanol-inducible and high-level expression in *Pichia pastoris*; and, the ZEOCIN resistance gene for positive selection in *E. coli* and *Pichia pastoris*. Plasmid pBK 119 was linearized with PineI before transforming into *Pichia pastoris* strains. Plasmid pBK was transformed into *Pichia pastoris* strain yJC53, a wild-type strain, and various PMT knockout strains.

PMT knockout yeast strains were created in *Pichia pastoris* following the procedure outlined for *Saccharomyces cerevisiae* in Gentzsch and Tanner, EMBO J. 1996 Nov. 1; 15(21): 25752-5759). The *Pichia pastoris* PMT genes were identified in the nucleotide sequence of the *Pichia pastoris* genome obtained from Integrated Genomics, Chicago, Ill. by homology searching using the nucleotide sequences for the *Saccharomyces cerevisiae* PMT genes. Deletion of *Pichia pastoris* PMT (PpPMT genes was as follows. The PpPMT deletion alleles were generated by the PCR overlap method (See for example, Davidson et al., 2004, Glycobiology 14:399-407; Ho et al., 1989, Gene 77:51-9; Horton et al., 1989, Gene 77:61-8). In the first PCR reaction, DNA comprising the nucleotide sequences for 5' and 3' flanking regions of the PMT genes and the NAT or HYG resistance markers (Goldstein and McCusker, 1999, Yeast 14:1541-1553; Goldstein et al., 1999, Yeast 15:507-110) were PCR amplified. The primers sequences for the regions flanking the PMT genes were designed using the *Pichia pastoris* genome nucleotide sequence obtained from Integrated Genomics, Chicago, Ill. as a guide. *Pichia pastoris* genomic DNA was used as a template for the PpPMT flanking regions PCR amplification, while NAT and HYG fragments were PCR amplified using plasmids as described in (Goldstein and McCusker, 1999, ibid.; Goldstein et al., 1999, ibid.) as templates. Then, in a second PCR reaction, all three first round PCR products were used as templates to generate an overlap product that contained all three fragments as a single linear allele. The final PCR product was then directly employed for transformation. Transformants were selected on YPD medium containing 200 µg/mL of hygromycin or 100 µg/mL of nourseothricin. In each case the proper integration of the mutant allele was confirmed by PCR. The PMT knockout strains created were yJC51 (pmt3Δ, pmt5Δ,pmt6Δ,), yJC55 (pmt1Δ), yJC66 (pmt2Δ), and yJC65 (pmt4Δ). The PMT knockout strains were each transformed with plasmid pBK119 encoding the above Kringle 1-3 protein.

Kringle 1-3 protein expression for the transformed yeast strains was carried out at in shake flasks at 24° C. with buffered glycerol-complex medium (BMGY) consisting of 1% yeast extract, 2% peptone, 100 mM potassium phosphate buffer pH 6.0, 1.34% yeast nitrogen base, 4×10-5% biotin, and 1% glycerol. The induction medium for protein expression was buffered methanol-complex medium (BMMY) consisting of 1% methanol instead of glycerol in BMGY. Pmt inhibitor Pmti-1, Pmti-2, or Pmti-3 in methanol was added to the growth medium to a final concentration of 0.2 µM, 2 µM, or 20 µM at the time the induction medium was added. Cells were harvested and centrifuged at 2,000 rpm for five minutes. The Pmt inhibitors Pmti-1, Pmti-2, and Pmti-3 are essentially interchangeable, with small variations in ease of use. For example, in the cell culture conditions described, the solubility of Pmti-3 is greater than that of Pmti-1 and Pmti-2 and, therefore, the most desirable of the three.

Seven µL of the supernatant from the yJC53 cultures treated with Pmti-1 or yJC55 was separated by polyacrylamide gel electrophoresis (SDS-PAGE) according to Laemmli, U. K. (1970) Nature 227, 680-685 and then electroblotted onto nitrocellulose membranes (Schleicher & Schuell (now Whatman, Inc., Florham Park, N.J.). Kringle 1-3 protein was detected on the Western blots using an anti-His antibody (H-15) from Santa Cruz Biotechnology Inc. (Santa Cruz, Calif.) and developed using the ImmunoPure Metal Enhanced DAB Substrate Kit (Pierce Biotechnology, Rockford, Ill.). As shown in Lane 1 of the Western blot shown in FIG. 1, Kringle 1-3 protein from untreated *Pichia pastoris* runs as a smear due to the presence of O-glycosylation. However, in contrast, Kringle 1-3 protein from yJC53 (*Pichia pastoris* treated with 2 or 20 µM Pmti-1, lanes 2 and 3, respectively) exhibits a distinct band, due to lack of O-glycosylation, similar to that of Kringle 1-3 protein expressed from yJC55 (a pmt1Δ knockout mutant of *Pichia pastoris*) (lanes 4 and 5). FIG. 1 further shows that Pmti-1 reduced O-glycosylation to a level similar to that observed in a strain lacking Pmt1.

To measure O-glycosylation reduction by the Pmt inhibitors, the Kringle 1-3 protein was purified from the growth medium using nickel chelation chromatography (Choi et al., 2003, Proc. Natl. Acad. Sci. U.S.A. 100(9): 5022-5027) and the O-glycans released from and separated from Kringle 1-3 protein by alkaline elimination (beta-elimination) (Harvey, 1999 Mass Spectrometry Reviews 18, 349-451). This process also reduces the newly formed reducing terminus of the released O-glycan (either oligomannose or mannose) to mannitol. The mannitol group thus serves as a unique indicator of each O-glycan. 0.5 nmole or more of Kringle 1-3 protein, contained within a volume of 100 µL PBS buffer, was required for beta elimination. The sample was treated with 25 µL alkaline borohydride reagent and incubated at 50° C. for 16 hours. About 20 µL arabitol internal standard was added, followed by 10 µL glacial acetic acid. The sample was then centrifuged through a Millipore filter containing both SEPA-BEADS and AG 50W—X8 resin and washed with water. The samples, including wash, were transferred to plastic autosampler vials and evaporated to dryness in a centrifugal evaporator. 150 µl 1% AcOH/MeOH was added to the samples and the samples evaporated to dryness in a centrifugal evaporator. This last step was repeated five more times. 200 µL of water was added and 100 µL of the sample was analyzed by high pH anion-exchange chromatography coupled with pulsed electrochemical detection-Dionex HPLC (HPAEC-PAD). Average O-glycan occupancy was determined based upon the amount of mannitol recovered. The results are summarized in Table 1, which shows that any one of the Pmt chemical inhibitors reduced O-linked glycosylation of secreted Kringle 1-3 protein in the *Pichia pastoris* strains that contained intact PMT1 and PMT2 genes to a level that was comparable to the level of O-linked glycosylation seen for cells containing deletions of either the PMT1 or PMT2 gene. Table 1 also shows that while the protein has two potential mammalian O-linked glycosylation sites, in yeast the protein has about 20 O-linked glycosylation sites.

TABLE 1

| Strain | Relevant Genotype | Treatment | O-Glycan Occupancy[1] |
|---|---|---|---|
| yJC53 | Wild-Type | 0 | 20 |
| | | 2 µM Pmti-1 | 9 |
| yJC51 | pmtΔ3, Δ5, Δ6 | 0 | 17 |
| | | 2 µM Pmti-1 | 6 |
| | | 20 µM Pmti-1 | 4 |
| | | 0.2 µM Pmti-2 | 3 |
| | | 2 µM Pmti-2 | 2 |
| | | 0.2 µM Pmti-3 | 6 |
| | | 2 µM Pmti-3 | 4 |
| yJC55 | pmtΔ1 | 0 | 3 |
| | | 2 µM Pmti-1 | 2 |
| | | 20 µM Pmti-1 | 2 |
| yJC66 | pmtΔ2 | 0 | 4 |
| | | 2 µM Pmti-1 | 4 |
| | | 20 µM Pmti-1 | 4 |
| yJC65 | pmtΔ4 | 0 | 18 |
| | | 2 µM Pmti-1 | 7 |
| | | 20 µM Pmti-1 | 4 |

[1]average number of O-linked mannose chains per protein.

EXAMPLE 3

In this example, yeast cells transformed with DNA encoding the *T. reesei* α-mannosidase results in production of proteins with reduced O-glycosylation and that the O-glycosylation was further reduced when the cells were also incubated in the presence of a Pmt inhibitor.

The H+L chains of an anti-Her2 monoclonal antibody were expressed in *Pichia pastoris* strains GS115 (WT) and GS115 that was genetically engineered to co-expressed *T. reesei* α-mannosidase (+Trman). GS115 is available from Invitrogen (Carlsbad, Calif.) and, with the exception of a HIS4 mutation to enable his4 selection, has an essentially wild type phenotype. The H+L chains were expressed as two separate genes from plasmid pJC284, which was derived from Invitrogen plasmid pAO815.

The H+L genes were generated using anti-Her2 antibody sequences obtained from GenBank. The GenBank accession number for the L chain is 1N8Z_A and the GenBank accession number for the H chain variable region plus CH1 domain is 1N8Z_B. The GenBank accession number for the H chain Fc region is BC092518. Both the H and L chain DNA sequences were codon optimized according to *Pichia pastoris* codon usage to enhance translation in *Pichia pastoris*. Optimization of codons for use in *Pichia* sp. is well known in the art and has been described in, for example, Outchkourov et al., 2002,Protein Expr. Purif. 24:18-24; Sharp and Li, 1987, Nucleic Acids Res. 15:1281-95; Woo J H, Liu et al., 2002, Protein Expression and Purification 25:270-282, and, Nakamura, et al., 2000, Nucleic Acids Res. 28:292. Constant regions of the H chain (human IgG1) and L chain (human Kappa) were synthesized by GeneArt Inc., Regensburg, Germany. Variable regions were made in-house using oligonucleotides purchased from IDT Inc. (Coralville, Iowa) in an overlapping PCR method. Full length H and L chains were assembled by overlapping PCR, and resulting H and L chains were cloned into pCR2.1 TOPO vector (Invitrogen, La Jolla, Calif.) to generate pDX344 and pDX349, respectively. H+L chains from pDX344 and pDX349 were combined with GAPDH promoters and AOX1 terminator sequences in vector pDX580 (backbone derived from Invitrogen vector pGAPZA). Finally, the H+L chain expression cassettes were subcloned from pDX580 into vector pJC284. The nucleotide sequence of the codon-optimized DNA encoding the light chain is shown in SEQ ID NO:7 and the nucleotide sequence of the codon-optimized DNA encoding the heavy chain is shown in SEQ ID NO:8. Plasmid pJC284 has GAPDH promoters for expressing the H+L genes and an intact his4 gene for selection of transformants in strain GS115 and GS115(+Trman). Yeast strains GS115 and GS115(+Trman) were transformed with pJC285 and transformants with the plasmid integrated into the genome at the his4 locus were isolated to produce strains that produced the anti-Her2 antibody.

Construction of strain GS115(+Trman) was as follows. The *Trichoderma reesei* α-1,2-mannosidase was expressed from an expression cassette in plasmid pJC285. Plasmid pJC285 was derived from Invitrogen vector pGAPZA, which has the Zeocin resistant gene as the selectable marker, and contains an expression cassette comprising DNA encoding the *T. reesei* α-1,2-mannosidase catalytic domain (SEQ ID NO:9) with the first 84 base pairs encoding its signal sequence replaced with a DNA encoding the *Saccharomyces cerevisiea* αMAT pre signal sequence (SEQ ID NO:10), which encodes just the ER-targeting amino acids, operably linked to DNA comprising the *Pichia pastoris* GAPH promoter (SEQ ID NO: 11) at the 5' end and DNA comprising the *Pichia pastoris* AOX1 transcription termination sequence (SEQ ID NO: 12) at the 3' end. The nucleotide sequence of the complete expression cassette is set forth in SEQ ID NO: 13. Yeast strain GS115 was transformed with pJC285 and transformants with the plasmid integrated into the genome at the GAPDH locus were isolated to produce strain GS115(+Trman).

Duplicate cultures of the strains were cultured in 200 mL of buffered dextrose-complex medium (BMDY) consisting of 1% yeast extract, 2% peptone, 100 mM potassium phosphate pH 6.0, 1.34% Yeast Nitrogen Base, 0.00004% biotin, 2% dextrose, and with or without Pmti-2 at 0.3 or 0.03 µM. Following 72 hours of growth, culture supernatants were collected and centrifuged to remove yeast cells. Antibody in the remaining supernatant fraction (about 200 mL) was purified over a Protein A column and subjected to O-glycan analysis as described in Example 2. In addition to the mannitol assay, the average length of O-linked mannose chains was determined by chromatographic analysis without hydrolysis. The results are summarized in Table 2.

There are 14 yeast O-glycan sites on the antibody. When the antibody was produced in the wild-type GS115 strain, all 14 O-glycan sites have glycan structures with 8% of the sites having just one mannose, 39% having a two mannose chain, 43% having a three mannose chain, and 9% having a four mannose chain (See Table 2). However, when the antibody was produced in wild-type cells treated with the chemical inhibitor Pmti-2, only two of the 14 O-glycan sites were occupied and for 76% of the two sites, the mannose chain had only one mannose residue. Neither of the two sites had a mannose chain with three or four mannose residues. It should be noted that the analysis did not determine which two of the 14 sites were occupied. Either any combination of two O-glycan sites per antibody molecule were occupied or particular-O-glycan sites are preferentially occupied. In the latter case, to provide antibodies (or other proteins) completely devoid of O-glycans, the amino acid sequences comprising the preferred O-glycan sites can be modified to amino acid sequences that eliminates O-linked glycosylation at the sites.

Table 2 further shows that when the antibody was produced in cells that included DNA encoding the *Tricoderma reesei* α-1,2-mannosidase (strain GS115(+Trman)), only four of the 14 O-glycan sites were occupied and for 95% of the four sites, the mannose chain had only one mannose residue. None of the four sites had a mannose chain with three or four mannose residues. If particular sites are preferentially O-glycosylated, to provide antibodies (or other proteins) completely devoid of O-glycans, the amino acid sequences comprising the preferred O-glycan sites can be modified to amino acid sequences that eliminates O-glycosylation at the sites.

Finally, Table 2 shows that when the antibody was produced in cells that included DNA encoding the *Tricoderma reesei* α-1,2-mannosidase and in the presence of Pmti-2, only one of the 14 O-glycan sites was occupied and for 91% of the sites, the mannose chain had only one mannose residue. No mannose chain had three or four mannose residues. If only one or only a few sites are preferentially O-glycosylated, to provide antibodies (or other proteins) completely devoid of O-glycans, the amino acid sequences comprising the preferred O-glycan sites can be modified to amino acid sequences that eliminate O-glycosylation at the sites Table 2 further shows that 0.3 uM of Pmti inhibitor is sufficient to reduced the occupancy by about 86% and the chain length for 76% of the molecules to one mannose while allowing the culture to grow. Including the *Tricoderma reesei* α-1,2-mannosidase allowed the amount of Pmti inhibitor to be reduced by 10 fold and the occupancy reduced to 93% and the chain length for 87% of the molecules to one mannose. These results show that using an amount of Pmti inhibitor that does not kill the cells is sufficient to produce glycoproteins having reduced O-linked glycosylation. These results further show that the Pmti inhibitor and the α-mannosidase appear to synergistically reduce the amount of O-linked glycosylation.

TABLE 2

| Strain | Occupancy | Man1 | Man2 | Man3 | Man4 |
|---|---|---|---|---|---|
| GS115 | 14 | 8 | 39 | 43 | 9 |
| GS115 + 0.3 µM Pmti-2 | 2 | 76 | 24 | 0 | 0 |
| GS115(+Trman) | 4 | 95 | 5 | 0 | 0 |
| GS115(+Trman) + 0.3 µM Pmti-2 | 1 | 91 | 9 | 0 | 0 |
| GS115(+Trman) + 0.03 µM Pmti-2 | 1 | 87 | 13 | 0 | 0 |

Figure 2:
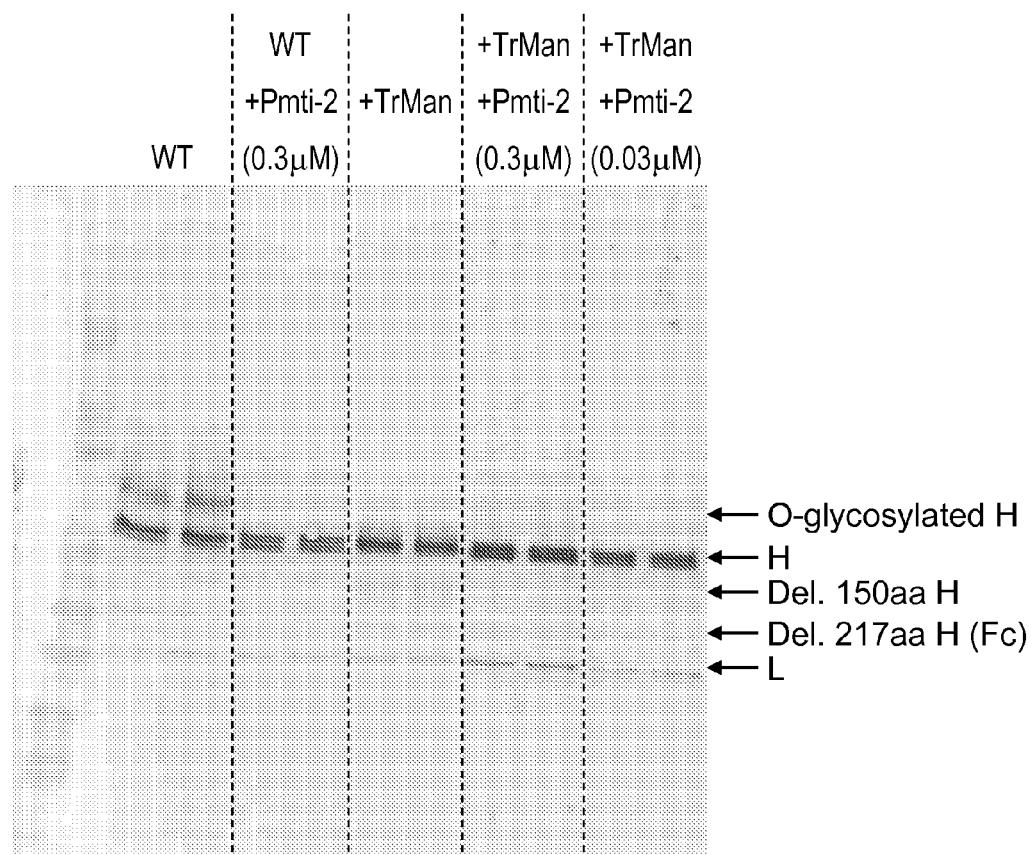
FIG. 2 shows a Western blot that demonstrates the effect of *T. reesei* α-mannosidase and the chemical inhibitor Pmti-2 on the O-glycosylation of immunoglobulin light and heavy chain polypeptides. Both *T. reesei* α-mannosidase and chemical Pmt inhibitors reduced the level of O-glycosylation.

Seven µL of the supernatant for each of the above were reduced and subjected to SDS-PAGE and Western blotting using an HRP-conjugated anti-human IgG (H&L) to detect H and L chains. The results are shown in FIG. 2. The hyper O-glycosylated H chain is the slowest migrating band visible in the first pair of lanes in FIG. 2. FIG. 2 shows that there is a decrease in the amount of O-glycosylated heavy chain when the antibody was coexpressed with *Tricoderma reesei* α-1,2-mannosidase or the cells expressing the antibody was incubated in the presence of the Pmti-2 inhibitor, or when the antibody was coexpressed with Tricoderma reesei α-1,2-mannosidase and the cells expressing both proteins was incubated in the presence of the Pmti-2 inhibitor.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

What is claimed is:

1. A method of producing a protein having reduced O-linked glycosylation comprising:

(a) providing a nucleic acid encoding a protein operably linked to an inducible promoter;

(b) introducing the nucleic acid into a yeast host cell or filamentous fungal host cell to provide a culture of the host cell;

(c) growing the culture for a time sufficient to provide a multiplicity of the host cells having the nucleic acid before contacting the culture with one or more inhibitors of Pmt-mediated O-linked glycosylation;

(d) contacting the culture with an inducer of the promoter to induce expression of the protein at a time before or at the same time as contacting the culture with the one or more inhibitors of Pmt-mediated O-linked glycosylation; and (e) isolating the glycoprotein produced by the host cell in the presence of the one or more inhibitors to produce the protein having reduced O-linked glycosylation.

2. The method of claim 1 wherein the one or more inhibitors is a benzylidene thiazolidinedione.

3. The method of claim 2 wherein the one or more inhibitors are selected from the group consisting of: 5-[[3,4-bis(phenylmethoxy)phenyl]methylene]-4-oxo-2-thioxo-3-thiazolidineacetic Acid; 5-[[3-(1-Phenylethoxy)-4-(2-phenylethoxy)]phenyl]methylene]-4-oxo-2-thioxo-3-thiazolidineacetic Acid; and 5-[[3-(1-Penyl-2-hydroxy)ethoxy)-4-(2-phenylethoxy)]phenyl]methylene]-4-oxo-2-thioxo-3-thiazolidineacetic Acid.

4. The method of claim 1, wherein the host cell [is a yeast or filamentous fungal cell that] has been genetically modified to produce glycoproteins with a predominant N-glycan glycoform.

5. A method of producing a protein having reduced O-linked glycosylation comprising:
   (a) providing a nucleic acid encoding a protein operably linked to an inducible promoter;
   (b) introducing the nucleic acid into a yeast host cell or filamentous fungal host cell and growing the host cell containing the nucleic acid to produce a culture of the host cell for a time sufficient to provide a multiplicity of the host cells having the nucleic acid before contacting the culture with one or more inhibitors of Pmt-mediated O-linked glycosylation;
   (c) contacting the culture with [with one or both of]: (i) one or more inhibitors of Pmt-mediated O-linked glycosylation and optionally with (ii) one or more [one or more] of α-1,2-mannosidase enzymes; and
   (d) isolating the glycoprotein produced by the host cell in the presence of the one or more inhibitors and the one or more [one or more] optional α-1,2-mannosidase enzymes to produce the protein having reduced O-linked glycosylation.

6. The method of claim 5 wherein the culture is grown in the presence of the one or more inhibitors of Pmt-mediated O-linked glycosylation.

7. The method of claim 5 wherein a second nucleic acid encoding the one or more α-1,2-mannosidase enzymes is provided and [introducing] the second nucleic acid is introduced into the host cell.

8. The method of claim 5 wherein the one or more inhibitors is a benzylidene thiazolidinedione.

9. The method of claim 5 wherein the one or more inhibitors are selected from the group consisting of: 5-[[3,4-bis(phenylmethoxy)phenyl]methylene]-4-oxo-2-thioxo-3-thiazolidineacetic Acid; 5-[[3-(1-Phenylethoxy)-4-(2-phenylethoxy)]phenyl]methylene]-4-oxo-2-thioxo-3-thiazolidineacetic Acid; and 5-[[3-(1-Phenyl-2-hydroxy)ethoxy)-4-(2-phenylethoxy)]phenyl]methylene]-4-oxo-2-thioxo-3-thiazolidineacetic Acid.

10. The method of claim 5 wherein the α-1,2-mannosidase is from *Trichoderma reesei, Saccharomyces* sp., or *Aspergillus* sp.

11. The method of claim 5 wherein the α-1,2-mannosidase is from *Trichoderma reesei*.

12. The method of claim 5 wherein the host cell includes a second nucleic acid, which encodes the α-1,2-mannosidase, operably linked to an inducible promoter.

13. The method of claim 5, wherein the host cell is selected from the group consisting of *K. lactis, Pichia pastoris, Pichia methanolica*, and *Hansenula*.

14. The method of claim 5, wherein the host cell [is a yeast or filamentous fungal cell that] has been genetically modified to produce glycoproteins with a predominant N-glycan glycoform.

* * * * *

SEQUENCE LISTING

<160> NUMBER OF SEQ ID NOS: 13

<210> SEQ ID NO 1
<211> LENGTH: 288
<212> TYPE: PRT
<213> ORGANISM: Artificial Sequence
<220> FEATURE:
<223> OTHER INFORMATION: Kringle 1-3 protein

<400> SEQUENCE: 1

```
Ser Glu Cys Lys Thr Gly Asn Gly Lys Asn Tyr Arg Gly Thr Met Ser
 1               5                  10                  15

Lys Thr Lys Asn Gly Ile Thr Cys Gln Lys Trp Ser Ser Thr Ser Pro
             20                  25                  30

His Arg Pro Arg Phe Ser Pro Ala Thr His Pro Ser Glu Gly Leu Glu
         35                  40                  45

Glu Asn Tyr Cys Arg Asn Pro Asp Asn Asp Pro Gln Gly Pro Trp Cys
     50                  55                  60

Tyr Thr Thr Asp Pro Glu Lys Arg Tyr Asp Tyr Cys Asp Ile Leu Glu
 65                  70                  75                  80

Cys Glu Glu Glu Cys Met His Cys Ser Gly Glu Asn Tyr Asp Gly Lys
                 85                  90                  95

Ile Ser Lys Thr Met Ser Gly Leu Glu Cys Gln Ala Trp Asp Ser Gln
            100                 105                 110

Ser Pro His Ala His Gly Tyr Ile Pro Ser Lys Phe Pro Asn Lys Asn
        115                 120                 125

Leu Lys Lys Asn Tyr Cys Arg Asn Pro Asp Arg Glu Leu Arg Pro Trp
    130                 135                 140

Cys Phe Thr Thr Asp Pro Asn Lys Arg Trp Glu Leu Cys Asp Ile Pro
145                 150                 155                 160

Arg Cys Thr Thr Pro Pro Pro Ser Ser Gly Pro Thr Tyr Gln Cys Leu
                165                 170                 175

Lys Gly Thr Gly Glu Asn Tyr Arg Gly Asn Val Ala Val Thr Val Ser
            180                 185                 190

Gly His Thr Cys Gln His Trp Ser Ala Gln Thr Pro His Thr His Ser
        195                 200                 205

Arg Thr Pro Glu Asn Phe Pro Cys Lys Asn Leu Asp Glu Asn Tyr Cys
    210                 215                 220

Arg Asn Pro Asp Gly Lys Arg Ala Pro Trp Cys His Thr Thr Asn Ser
225                 230                 235                 240

Gln Val Arg Trp Glu Tyr Cys Lys Ile Pro Ser Cys Asp Ser Ser Pro
                245                 250                 255

Val Ser Thr Glu Gln Leu Ala Pro Thr Ala Pro Pro Glu Leu Thr Pro
            260                 265                 270

Val Val Gln Asp Gly Gly His His His His His His His His
        275                 280                 285
```

<210> SEQ ID NO 2
<211> LENGTH: 33
<212> TYPE: DNA
<213> ORGANISM: Artificial Sequence
<220> FEATURE:
<223> OTHER INFORMATION: forward primer K1-3/UP

<400> SEQUENCE: 2
cggaattctc agagtgcaag actgggaata gaa        33

```
<210> SEQ ID NO 3
<211> LENGTH: 39
<212> TYPE: DNA
<213> ORGANISM: Artificial Sequence
<220> FEATURE:
<223> OTHER INFORMATION: reverse primer K1-3/LP1

<400> SEQUENCE: 3
atgatgatga ccaccaccgt cctggaccac aggggttag                       39

<210> SEQ ID NO 4
<211> LENGTH: 39
<212> TYPE: DNA
<213> ORGANISM: Artificial Sequence
<220> FEATURE:
<223> OTHER INFORMATION: reverse primer K1-3/LP2

<400> SEQUENCE: 4
ttaatgatga tgatgatgat gatgatgatg accaccacc                       39

<210> SEQ ID NO 5
<211> LENGTH: 36
<212> TYPE: DNA
<213> ORGANISM: Artificial Sequence
<220> FEATURE:
<223> OTHER INFORMATION: forward primer K3f (Asn to Ser)

<400> SEQUENCE: 5
acccctcaca cacattctag gacaccagaa aacttc                          36

<210> SEQ ID NO 6
<211> LENGTH: 27
<212> TYPE: DNA
<213> ORGANISM: Artificial Sequence
<220> FEATURE:
<223> OTHER INFORMATION: reverse primer K3r

<400> SEQUENCE: 6
ctgtgcactc cagtgctgac aggtgtg                                    27

<210> SEQ ID NO 7
<211> LENGTH: 645
<212> TYPE: DNA
<213> ORGANISM: Artificial Sequence
<220> FEATURE:
<223> OTHER INFORMATION: Codon-optimized sequence encoding light chain

<400> SEQUENCE: 7
gacattcaga tgacacagtc tccatcttct ttgtccgctt ccgtcggtga tagagttact    60
atcacctgta gagcttccca agacgtcaac accgctgtcg cctggtacca acagaagcca   120
ggtaaggctc caaaactttt gatctactct gcctctttct gtactccgg tgttccatcc    180 agattttctg gttctagatc cggtaccgac ttcaccttga ccatctcttc cttgcaacca   240
gaagacttcg ctacctacta ctgtcaacaa cactacacta ctcctccaac tttcggtcaa   300
ggaactaagg ttgagattaa agaaactgtt gctgctccat ccgttttcat tttcccacca   360
tccgacgaac aattgaagtc tggtacagct tccgttgttt gtttgttgaa caacttctac   420
ccaagagagg ctaaggttca gtggaaggtt gacaacgctt tgcaatccgg taactcccaa   480
gaatccgtta ctgagcagga ttctaaggat tccacttact ccttgtcctc cactttgact   540
ttgtccaagg ctgattacga aagcacaag gtttacgcat gcgaggttac acatcagggt   600
ttgtcctccc cagttactaa gtccttcaac agaggagagt gttaa                   645
```

<210> SEQ ID NO 8
<211> LENGTH: 1353
<212> TYPE: DNA
<213> ORGANISM: Artificial Sequence
<220> FEATURE:
<223> OTHER INFORMATION: Codon-optimized sequence encoding heavy chain

<400> SEQUENCE: 8

```
gaggtccaat tggttgaatc tggtggaggt ttggtccaac caggtggatc tctgagactt      60
tcttgtgctg cctctggttt caacattaag gatacttaca tccactgggt tagacaggct    120
ccaggtaagg gtttggagtg ggttgctaga atctacccaa ccaacggtta caccagatac    180
gctgattccg ttaagggtag attcaccatt tccgctgaca cttccaagaa cactgcttac    240
ttgcaaatga actctttgag agctgaggac actgccgtct actactgttc agatggggt    300 ggtgacggtt tctacgccat ggactactgg ggtcaaggta ccttggttac tgtctcttcc    360
gcttctacta agggaccatc cgttttttcca ttggctccat cctctaagtc tacttccggt    420
ggtactgctg ctttgggatg tttggttaag gactacttcc cagagcctgt tactgttttct    480 tggaactccg gtgctttgac ttctggtgtt cacacttttcc cagctgtttt gcaatcttcc    540 ggttttgtact ccttgtcctc cgttgttact gttccatcct cttccttggg tactcagact    600
tacatctgta acgttaacca caagccatcc aacactaagg ttgacaagaa ggttgagcca    660
aagtcctgtg acaagacaca tacttgtcca ccatgtccag ctccagaatt gttgggtggt    720
ccatccgttt tcttgttccc accaaagcca aaggacactt tgatgatctc cagaactcca    780
gaggttacat gtgttgttgt tgacgtttct cacgaggacc cagaggttaa gttcaactgg    840
tacgttgacg gtgttgaagt tcacaacgct aagactaagc caagagagga gcagtacaac    900
tccacttaca gagttgttc cgttttgact gttttgcacc aggattggtt gaacggaaag    960
gagtacaagt gtaaggtttc caacaaggct ttgccagctc caatcgaaaa gactatctcc    1020
aaggctaagg gtcaaccaag agagccacag gtttacactt tgccaccatc cagagatgag    1080
ttgactaaga accaggtttc cttgacttgt ttggttaaag gattctaccc atccgacatt    1140
gctgttgagt gggaatctaa cggtcaacca gagaacaact acaagactac tccaccagtt    1200
ttggattctg acggttcctt cttccttgtac tccaagttga ctgttgacaa gtccagatgg    1260
caacagggta cgttttctc ctgttccgtt atgcatgagg ctttgcacaa ccactacact    1320
caaaagtcct tgtctttgtc cccaggtaag taa                                  1353
```

<210> SEQ ID NO 9
<211> LENGTH: 500
<212> TYPE: DNA
<213> ORGANISM: Artificial Sequence
<220> FEATURE:
<223> OTHER INFORMATION: Pichia pastoris GAPDH promoter

<400> SEQUENCE: 9

```
agatctttt tgtagaaatg tcttggtgtc ctcgtccaat caggtagcca tctctgaaat      60
atctggctcc gttgcaactc cgaacgacct gctggcaacg taaaattctc cggggtaaaa    120
cttaaatgtg gagtaatgga accagaaacg tctcttccct tctctctcct tccaccgccc    180
gttaccgtcc ctaggaaatt ttactctgct ggagagcttc ttctacggcc cccttgcagc    240
aatgctcttc ccagcattac gttcgggta aaacggaggt cgtgtacccg acctagcagc    300
ccagggatgg aaaagtcccg gccgtcgctg gcaataatag cgggcggacg catgtcatga    360
gattattgga aaccaccaga atcgaatata aaaggcgaac acctttccca atttttggttt    420
```

```
ctcctgaccc aaagacttta aatttaatttt atttgtccct atttcaatca attgaacaac    480
tatttcgaaa cgagggaatt                                                 500

<210> SEQ ID NO 10
<211> LENGTH: 57
<212> TYPE: DNA
<213> ORGANISM: Artificial Sequence
<220> FEATURE:
<223> OTHER INFORMATION: Saccharomyces cerevisiea alpha-MAT pre signal
      sequence

<400> SEQUENCE: 10
atgagatttc cttcaatttt tactgctgtt ttattcgcag catcctccgc attagct        57

<210> SEQ ID NO 11
<211> LENGTH: 1494
<212> TYPE: DNA
<213> ORGANISM: Artificial Sequence
<220> FEATURE:
<223> OTHER INFORMATION: Tricoderma reesei alph-1,2-mannosidase
      catalytic domain

<400> SEQUENCE: 11
cgcgccggat ctcccaaccc tacgagggcg gcagcagtca aggccgcatt ccagacgtcg     60
tggaacgctt accaccattt tgcctttccc catgacgacc tccacccggt cagcaacagc    120
tttgatgatg agagaaacgg ctggggctcg tcggcaatcg atggcttgga cacggctatc    180
ctcatggggg atgccgacat tgtgaacacg atccttcagt atgtaccgca gatcaacttc    240
accacgactg cggttgccaa ccaaggcatc tccgtgttcg agaccaacat tcggtacctc    300
ggtggcctgc tttctgccta tgacctgttg cgaggtcctt tcagctcctt ggcgacaaac    360
cagaccctgg taaacagcct tctgaggcag gctcaaacac tggccaacgg cctcaaggtt    420
gcgttcacca ctcccagcgg tgtcccggac cctaccgtct tcttcaaccc tactgtccgg    480
agaagtggtg catctagcaa caacgtcgct gaaattggaa gcctggtgct cgagtggaca    540
cggttgagcg acctgacggg aaacccgcag tatgcccagc ttgcgcagaa gggcgagtcg    600
tatctcctga atccaagggg aagcccggag gcatggcctg gctgattgg aacgtttgtc     660 agcacgagca acggtacctt tcaggatagc agcggcagct ggtccggcct catggacagc    720
ttctacgagt acctgatcaa gatgtacctg tacgacccgg ttgcgtttgc acactacaag    780
gatcgctggg tccttgctgc cgactcgacc attgcgcatc tcgcctctca cccgtcgacg    840
cgcaaggact tgaccttttt gtcttcgtac aacggacagt ctacgtcgcc aaactcagga    900
catttggcca gttttgccgg tggcaacttc atcttgggag cattctcct gaacgagcaa    960 aagtacattg actttggaat caagcttgcc agctcgtact ttgccacgta caaccagacg    1020
gcttctggaa tcggcccgga aggcttcgcg tgggtggaca cgtgacgggc gccggcggc    1080 tcgccgccct cgtcccagtc cgggttctac tcgtcggcag gattctgggt gacggcaccg    1140
tattacatcc tgcggccgga gacgctggag agcttgtact acgcataccg cgtcacgggc    1200
gactccaagt ggcaggacct ggcgtgggaa gcgttcagtg ccattgagga cgcatgccgc    1260
gccggcagcg cgtactcgtc catcaacgac gtgacgcagg ccaacggcgg gggtgcctct    1320
gacgatatgg agagcttctg gtttgccgag cgctcaagt atgcgtacct gatctttgcg     1380
gaggagtcga tgtgcaggt gcaggccaac ggcgggaaca aatttgtctt taacacggag     1440
gcgcacccct ttagcatccg ttcatcatca cgacggggcg gccaccttgc ttaa          1494
```

<210> SEQ ID NO 12
<211> LENGTH: 486
<212> TYPE: DNA
<213> ORGANISM: Artificial Sequence
<220> FEATURE:
<223> OTHER INFORMATION: Pichia pastoris AOX1 transcription termination
      sequence

<400> SEQUENCE: 12

```
aagggcgaat tcaattcacg tggcccagcc ggccgtctcg gatcggtacc tcgagccgcg       60
gcggccgcca gcttgggccc gaacaaaaac tcatctcaga agaggatctg aatagcgccg      120
tcgaccatca tcatcatcat cattgagttt tagccttaga catgactgtt cctcagttca      180
agttgggcac ttacgagaag accggtcttg ctagattcta atcaagagga tgtcagaatg      240
ccatttgcct gagagatgca ggcttcattt ttgatacttt tttatttgta acctatatag      300
tataggattt tttttgtcat tttgtttctt ctcgtacgag cttgctcctg atcagcctat      360
ctcgcagctg atgaatatct tgtggtaggg gtttgggaaa atcattcgag tttgatgttt      420
ttcttggtat ttcccactcc tcttcagagt acagaagatt aagtgagacc ttcgtttgtg      480
cggatc                                                                 486
```

<210> SEQ ID NO 13
<211> LENGTH: 2550
<212> TYPE: DNA
<213> ORGANISM: Artificial Sequence
<220> FEATURE:
<223> OTHER INFORMATION: Tricoderma reesei alpha-1,2-mannosidase
      expression cassette
<220> FEATURE:
<221> NAME/KEY: promoter
<222> LOCATION: (1)...(507)
<223> OTHER INFORMATION: GAPDH promoter sequence
<220> FEATURE:
<221> NAME/KEY: sig_peptide
<222> LOCATION: (508)...(564)
<223> OTHER INFORMATION: encodes Saccharomyces cerevisiea alpha-MAT
      pre signal sequence
<220> FEATURE:
<221> NAME/KEY: CDS
<222> LOCATION: (565)...(2058)
<223> OTHER INFORMATION: encodes Tricoderma reesei alpha-1,2-
      mannosidase catalytic domain
<220> FEATURE:
<221> NAME/KEY: terminator
<222> LOCATION: (2065)...(2550)
<223> OTHER INFORMATION: Pichia pastoris AOX1 transcription
      termination sequence

<400> SEQUENCE: 13

```
agatctttt tgtagaaatg tcttggtgtc ctcgtccaat caggtagcca tctctgaaat        60
atctggctcc gttgcaactc cgaacgacct gctggcaacg taaaattctc cggggtaaaa      120
cttaaatgtg gagtaatgga accagaaacg tctcttccct tctctctcct tccaccgccc      180
gttaccgtcc ctaggaaatt ttactctgct ggagagcttc ttctacggcc cccttgcagc      240
aatgctcttc ccagcattac gttgcgggta aaacggaggt cgtgtacccg acctagcagc      300
ccagggatgg aaaagtcccg gccgtcgctg gcaataatag cgggcggacg catgtcatga      360
gattattgga accaccaga atcgaatata aaaggcgaac acctttccca attttggttt       420
ctcctgaccc aaagacttta aatttaattt atttgtccct atttcaatca attgaacaac      480
tatttcgaaa cgagggaatt cgaaacg atg aga ttt cct tca att ttt act gct      534
                                  Met Arg Phe Pro Ser Ile Phe Thr Ala
                                                                -15
```

```
gtt tta ttc gca gca tcc tcc gca tta gct cgc gcc gga tct ccc aac     582
Val Leu Phe Ala Ala Ser Ser Ala Leu Ala Arg Ala Gly Ser Pro Asn
-10             -5                   1               5 cct acg agg gcg gca gca gtc aag gcc gca ttc cag acg tcg tgg aac     630
Pro Thr Arg Ala Ala Ala Val Lys Ala Ala Phe Gln Thr Ser Trp Asn
             10              15                  20 gct tac cac cat ttt gcc ttt ccc cat gac gac ctc cac ccg gtc agc     678
Ala Tyr His His Phe Ala Phe Pro His Asp Asp Leu His Pro Val Ser
         25              30              35 aac agc ttt gat gat gag aga aac ggc tgg ggc tcg tcg gca atc gat     726
Asn Ser Phe Asp Asp Glu Arg Asn Gly Trp Gly Ser Ser Ala Ile Asp
     40              45              50 ggc ttg gac acg gct atc ctc atg ggg gat gcc gac att gtg aac acg     774
Gly Leu Asp Thr Ala Ile Leu Met Gly Asp Ala Asp Ile Val Asn Thr
55              60              65              70 atc ctt cag tat gta ccg cag atc aac ttc acc acg act gcg gtt gcc     822
Ile Leu Gln Tyr Val Pro Gln Ile Asn Phe Thr Thr Thr Ala Val Ala
         75              80              85 aac caa ggc atc tcc gtg ttc gag acc aac att cgg tac ctc ggt ggc     870
Asn Gln Gly Ile Ser Val Phe Glu Thr Asn Ile Arg Tyr Leu Gly Gly
             90              95             100 ctg ctt tct gcc tat gac ctg ttg cga ggt cct ttc agc tcc ttg gcg     918
Leu Leu Ser Ala Tyr Asp Leu Leu Arg Gly Pro Phe Ser Ser Leu Ala
         105             110             115 aca aac cag acc ctg gta aac agc ctt ctg agg cag gct caa aca ctg     966
Thr Asn Gln Thr Leu Val Asn Ser Leu Leu Arg Gln Ala Gln Thr Leu
    120             125             130 gcc aac ggc ctc aag gtt gcg ttc acc act ccc agc ggt gtc ccg gac    1014
Ala Asn Gly Leu Lys Val Ala Phe Thr Thr Pro Ser Gly Val Pro Asp
135             140             145             150 cct acc gtc ttc ttc aac cct act gtc cgg aga agt ggt gca tct agc    1062
Pro Thr Val Phe Phe Asn Pro Thr Val Arg Arg Ser Gly Ala Ser Ser
             155             160             165 aac aac gtc gct gaa att gga agc ctg gtg ctc gag tgg aca cgg ttg    1110
Asn Asn Val Ala Glu Ile Gly Ser Leu Val Leu Glu Trp Thr Arg Leu
         170             175             180 agc gac ctg acg gga aac ccg cag tat gcc cag ctt gcg cag aag ggc    1158
Ser Asp Leu Thr Gly Asn Pro Gln Tyr Ala Gln Leu Ala Gln Lys Gly
         185             190             195 gag tcg tat ctc ctg aat cca aag gga agc ccg gag gca tgg cct ggc    1206
Glu Ser Tyr Leu Leu Asn Pro Lys Gly Ser Pro Glu Ala Trp Pro Gly
    200             205             210 ctg att gga acg ttt gtc agc acg agc aac ggt acc ttt cag gat agc    1254
Leu Ile Gly Thr Phe Val Ser Thr Ser Asn Gly Thr Phe Gln Asp Ser
215             220             225             230 agc ggc agc tgg tcc ggc ctc atg gac agc ttc tac gag tac ctg atc    1302
Ser Gly Ser Trp Ser Gly Leu Met Asp Ser Phe Tyr Glu Tyr Leu Ile
             235             240             245 aag atg tac ctg tac gac ccg gtt gcg ttt gca cac tac aag gat cgc    1350
Lys Met Tyr Leu Tyr Asp Pro Val Ala Phe Ala His Tyr Lys Asp Arg
         250             255             260 tgg gtc ctt gct gcc gac tcg acc att gcg cat ctc gcc tct cac ccg    1398
Trp Val Leu Ala Ala Asp Ser Thr Ile Ala His Leu Ala Ser His Pro
         265             270             275 tcg acg cgc aag gac ttg acc ttt ttg tct tcg tac aac gga cag tct    1446
Ser Thr Arg Lys Asp Leu Thr Phe Leu Ser Ser Tyr Asn Gly Gln Ser
    280             285             290 acg tcg cca aac tca gga cat ttg gcc agt ttt gcc ggt ggc aac ttc    1494
Thr Ser Pro Asn Ser Gly His Leu Ala Ser Phe Ala Gly Gly Asn Phe
295             300             305             310
```

```
atc ttg gga ggc att ctc ctg aac gag caa aag tac att gac ttt gga     1542
Ile Leu Gly Gly Ile Leu Leu Asn Glu Gln Lys Tyr Ile Asp Phe Gly
                315                 320                 325 atc aag ctt gcc agc tcg tac ttt gcc acg tac aac cag acg gct tct     1590
Ile Lys Leu Ala Ser Ser Tyr Phe Ala Thr Tyr Asn Gln Thr Ala Ser
                330                 335                 340 gga atc ggc ccc gaa ggc ttc gcg tgg gtg gac agc gtg acg ggc gcc     1638
Gly Ile Gly Pro Glu Gly Phe Ala Trp Val Asp Ser Val Thr Gly Ala
                345                 350                 355 ggc ggc tcg ccg ccc tcg tcc cag tcc ggg ttc tac tcg tcg gca gga     1686
Gly Gly Ser Pro Pro Ser Ser Gln Ser Gly Phe Tyr Ser Ser Ala Gly
            360                 365                 370 ttc tgg gtg acg gca ccg tat tac atc ctg cgg ccg gag acg ctg gag     1734
Phe Trp Val Thr Ala Pro Tyr Tyr Ile Leu Arg Pro Glu Thr Leu Glu
375                 380                 385                 390 agc ttg tac tac gca tac cgc gtc acg ggc gac tcc aag tgg cag gac     1782
Ser Leu Tyr Tyr Ala Tyr Arg Val Thr Gly Asp Ser Lys Trp Gln Asp
                395                 400                 405 ctg gcg tgg gaa gcg ttc agt gcc att gag gac gca tgc cgc gcc ggc     1830
Leu Ala Trp Glu Ala Phe Ser Ala Ile Glu Asp Ala Cys Arg Ala Gly
                410                 415                 420 agc gcg tac tcg tcc atc aac gac gtg acg cag gcc aac ggc ggg ggt     1878
Ser Ala Tyr Ser Ser Ile Asn Asp Val Thr Gln Ala Asn Gly Gly Gly
                425                 430                 435 gcc tct gac gat atg gag agc ttc tgg ttt gcc gag gcg ctc aag tat     1926
Ala Ser Asp Asp Met Glu Ser Phe Trp Phe Ala Glu Ala Leu Lys Tyr
                440                 445                 450 gcg tac ctg atc ttt gcg gag gag tcg gat gtg cag gtg cag gcc aac     1974
Ala Tyr Leu Ile Phe Ala Glu Glu Ser Asp Val Gln Val Gln Ala Asn
455                 460                 465                 470 ggc ggg aac aaa ttt gtc ttt aac acg gag gcg cac ccc ttt agc atc     2022
Gly Gly Asn Lys Phe Val Phe Asn Thr Glu Ala His Pro Phe Ser Ile
                475                 480                 485 cgt tca tca tca cga cgg ggc ggc cac ctt gct taa ttaaggaagg          2068
Arg Ser Ser Ser Arg Arg Gly Gly His Leu Ala *
                490                 495 gcgaattcaa ttcacgtggc ccagccggcc gtctcggatc ggtacctcga gccgcggcgg   2128
ccgccagctt gggcccgaac aaaaactcat ctcagaagag gatctgaata gcgccgtcga   2188
ccatcatcat catcatcatt gagttttagc cttagacatg actgttcctc agttcaagtt   2248
gggcacttac gagaagaccg gtcttgctag attctaatca agaggatgtc agaatgccat   2308
ttgcctgaga gatgcaggct tcattttga tactttttta tttgtaacct atatagtata    2368
ggattttttt tgtcattttg tttcttctcg tacgagcttg ctcctgatca gcctatctcg   2428
cagctgatga atatcttgtg gtaggggttt gggaaaatca ttcgagtttg atgttttct    2488 tggtatttcc cactcctctt cagagtacag aagattaagt gagaccttcg tttgtgcgga   2548
tc                                                                  2550
```